US008420852B2

(12) United States Patent
Dennis et al.

(10) Patent No.: US 8,420,852 B2
(45) Date of Patent: *Apr. 16, 2013

(54) PHOSPHOLIPASE A2 INHIBITORS AND THEIR USE IN TREATING NEUROLOGICAL INJURY AND DISEASE

(75) Inventors: Edward A. Dennis, La Jolla, CA (US); Daren Stephens, Morrisville, NC (US); Samuel David, Dorval (CA); Ruben Lopez-Vales, Catalonia (ES); Athena Kalyvas, Laval (CA); George Kokotos, Athens (GR); Violetta Constantinou-Kokotou, Athens (GR); Efrosini Barbayianni, Athens (GR); Victoria Magrioti, Athens (GR)

(73) Assignee: The Regents of the University of California, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/666,773

(22) PCT Filed: Jul. 3, 2008

(86) PCT No.: PCT/US2008/069257
§ 371 (c)(1),
(2), (4) Date: Jan. 4, 2011

(87) PCT Pub. No.: WO2009/009449
PCT Pub. Date: Jan. 15, 2009

(65) Prior Publication Data
US 2011/0105610 A1 May 5, 2011

Related U.S. Application Data

(60) Provisional application No. 60/948,423, filed on Jul. 6, 2007.

(51) Int. Cl.
*C07C 229/00* (2006.01)
*A01N 37/12* (2006.01)
*A01N 37/44* (2006.01)

(52) U.S. Cl.
USPC ............ 560/170; 562/567; 514/551; 514/563

(58) Field of Classification Search .................. None
See application file for complete search history.

(56) References Cited

U.S. PATENT DOCUMENTS
2005/0148549 A1 * 7/2005 Dennis et al. ................. 514/114

FOREIGN PATENT DOCUMENTS
WO    WO 95/19959    7/1995
WO    2007022443    * 2/2007
WO    WO 2007/022443 A2    2/2007

OTHER PUBLICATIONS

Kokotos et al., Journal of Medicinal Chemistry (2002), 45(14), 2891-2893.*

(Continued)

*Primary Examiner* — Karl J Puttlitz
(74) *Attorney, Agent, or Firm* — DLA Piper LLP (US)

(57) ABSTRACT

Phospholipase $A_2$ ($PLA_2$) forms are expressed in spinal cord whose inhibition induces a potent antihyperalgesia. $PLA_2$ inhibitor compounds are provided that include a common motif consisting of a 2-oxoamide with a hydrocarbon tail and a four carbon tether. The compounds block Group IVA calcium dependent $PLA_2$ ($cPLA_2$) and/or Group VIA calcium independent $PLA_2$ ($iPLA_2$) and/or Group V secreted $PLA_2$ ($sPLA_2$). Pharmaceutical compositions of compounds having $cPLA_2$ inhibitory activity (but not $iPLA_2$ or $sPLA_2$ inhibitory activity) are useful in treating multiple sclerosis, while compositions of compounds having $sPLA_2$ inhibitory activity (as well as $iPLA_2$ and $CPLA_2$ activity) are useful in treating spinal cord injuries (with related functional recovery).

11 Claims, 17 Drawing Sheets

OTHER PUBLICATIONS

Database Caplus Chemical Abstracts Service, Columbus, Ohio, US; Database Accession No. 2004:415199 Abstract of Lee et al., Journal of the Korean Chemical Society (2004), 48(2), 161-170.*
Kokotos et al., Journal of Medicinal Chemistry (2004), 47(14), 3615-3628.*
Farooqui et al., Pharmacol Rev 58:591-620, 2006.*
Kalyvas et al., Neuron, vol. 41, 323-335, 2004.*
Kokotos et al., "Novel 2-Oxoamide Inhibitors of Human Group IVA Phospholipase A2," *J. Med. Chem.* (2002), 45:2891-2893.

* cited by examiner

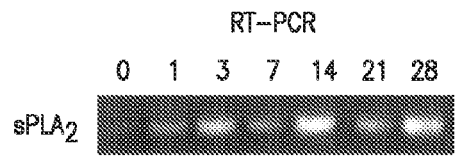
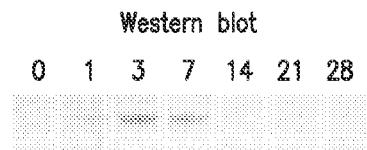
FIG. 1a
FIG. 1b
FIG. 1c
FIG. 1d
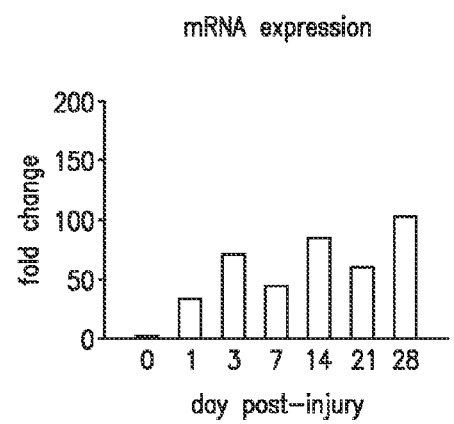
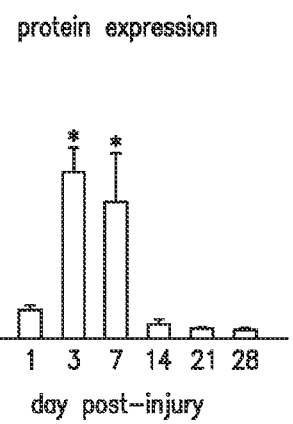
FIG. 2a
FIG. 2b

PHOSPHOLIPASE A2 INHIBITORS AND THEIR USE IN TREATING NEUROLOGICAL INJURY AND DISEASE

CROSS REFERENCE TO RELATED APPLICATIONS

This application is a 35 USC §371 National Stage application of International Application No. PCT/US2008/069257 filed Jul. 3, 2008, now pending; which claims the benefit under 35 USC §119(e) to U.S. Application Ser. No. 60/948,423 filed Jul. 6, 2007, now abandoned. The disclosure of each of the prior applications is considered part of and is incorporated by reference in the disclosure of this application.

BACKGROUND

Phospholipase $A_2$ ($PLA_2$) constitutes a super-family of enzymes that catalyze the hydrolysis of the fatty acid ester from the sn-2 position of membrane phospholipids, yielding a free fatty acid and a lysophospholipid. Among the intracellular $PLA_2$s are the cytosolic Group IVA $PLA_2$ (GIVA $PLA_2$, also referred to herein as $cPLA_2$), which is generally considered a pro-inflammatory enzyme; the calcium-independent Group VIA $PLA_2$ (GVIA $PLA_2$, also referred to herein as $iPLA_2$); and, secreted Group V $PLA_2$ ($sPLA_2$). GVIA $PLA_2$ is actually a group of cytosolic enzymes ranging from 85 to 88 kDa and expressed as several distinct splice variants of the same gene, only two of which have been shown to be catalytically active (Group VIA-1 and VIA-2 $PLA_2$); (Larsson, et al., *J. Biol. Chem.* 273: 207-214, 1998). The role of GVIA $PLA_2$ in the inflammatory process is unclear, but this enzyme appears to be the primary $PLA_2$ for basal metabolic functions within the cell, reportedly including membrane homeostasis (Balsinde, et al., *Proc. Natl. Acad. Sci. U.S.A.*, 92:8527-8531, 1995; Balsinde, et al., *J. Biol. Chem.*, 272: 29317-29321, 1997; Balsinde, et al., *J. Biol. Chem.*, 272:16069-16072, 1997; Ramanadham, et al., *J. Biol. Chem.*, 274:13915-13927, 1999; Birbes, et al., *Eur. J. Biochem.*, 267:7118-7127, 2000; and Ma, et al., *Lipids*, 36:689-700, 2001), insulin receptor signaling (Ramanadham, et al., *J. Biol. Chem.*, 274: 13915-13927, 1999; Ma, et al., *J. Biol. Chem.*, 276: 13198-13208, 2001) and calcium channel regulation. (Guo, et al., *J. Biol. Chem.*, 277: 32807-32814, 2002; Cummings et al., *Am. J. Physiol. Renal Physiol.*, 283: F492-498, 2002). GVIA, GIVA and GV $PLA_2$ are all present and play active roles in central nervous system inflammatory processes (see, e.g., Sun, et al., *J. Lipid Res.*, 45: 205-213, 2004).

The GVIA $PLA_2$ enzymes all contain a consensus lipase motif, Gly-Thr-Ser*-Thr-Gly, with the catalytic serine confirmed by site-directed mutagenesis (Larsson, et al., *J. Biol. Chem.*, 273:207-14, 1998; Tang, et al., *J. Biol. Chem.*, 272: 8567-8575, 2002). Other residues critical for catalysis have yet to be confirmed, and while the mechanism by which it cleaves the sn-2 linkage has not been established, GVIA $PLA_2$ is likely to be an hydrolase with a catalytic Ser/Asp dyad similar to Group IVA $PLA_2$ (Dessen, et al., *Cell* 1999, 97: 349-360, 1999; Dessen, *Biochim. Biophys. Acta*, 1488: 40-47, 2000; Phillips, et al., *J. Biol. Chem.*, 278: 41326-41332, 2003). Constitutive mRNA and protein have been detected in the spinal cord for group IVA calcium-dependent $PLA_2$ (Group IVA $cPLA_2$) and Group VIA calcium-independent $iPLA_2$ (Group VIA $iPLA_2$) and secretory Group II and V $sPLA_2$ forms (Lucas, et al., *Br. J. Pharmacol.*, 144:940-952, 2005, Svensson et al., *Annu. Rev. Pharmacol. Toxicol.*, 42:553-555, 2005).

The discovery of a novel structural series of 2-oxoamides that inhibit Group IVA $cPLA_2$ in vitro and in vivo (Kokotos, et al., *J. Med. Chem.*, 45:2891-2893, 2002; Kokotos, et al., *J. Med. Chem.*, 47:3615-3628, 2004) was recently reported. In that initial work, 2-oxoamides were observed to inhibit inflammation in the rat paw carrageenan-induced edema assay (Kokotos, et al., supra, 2004).

Based upon the similarity of substrates, classes of common inhibitors, very limited sequence homology in the region of the catalytic serine, and similarities in the active sites of GIVA and GVIA $PLA_2$, GIVA $PLA_2$ may show cross-reactivity with GVIA $PLA_2$. It has been difficult, therefore, to design GIVA and GVIA $PLA_2$ selective inhibitors that can distinguish between the molecules in vivo. Further, selective inhibitors for GV $PLA_2$ have been difficult to design. However, as the results reported herein demonstrate, inhibition to $PLA_2$ molecules can have surprisingly different consequences in vivo. $PLA_2$ inhibitors that are selective for particular targets can be used to advantage to treat disease processes related to $PLA_2$ metabolism. Here, the use of compounds specific for particular $PLA_2$ s is demonstrated in treating multiple sclerosis and spinal cord injury.

SUMMARY

The invention provides potent 2-oxoamide inhibitors of phospholipase $A_2$ ($PLA_2$), including ones selective for Group IVA $cPLA_2$ and/or Group VIA $iPLA_2$ and/or $sPLA_2$, as well as methods for use of the inhibitory compounds. As demonstrated herein, the $cPLA_2$ inhibitory compounds are especially useful in treating multiple sclerosis in an experimental autoimmune encephalitis (EAE) animal model thereof. In contrast, such inhibitory compounds can exert detrimental effects in an animal model of spinal cord injury (SCI), on which inhibitors of $sPLA_2$ have beneficial, therapeutic effect. Thus, the invention provides compounds that have differential inhibitory effects on $PLA_2$ enzymes, to differing therapeutic ends. The inhibitory compounds of the invention all act to the exclusion of the cyclooxygenase enzymes also involved in inflammation.

The $PLA_2$ inhibitors of the invention are 2-oxoamide compounds which exhibit a high degree of specificity for the cytosolic ($cPLA_2$) and/or calcium-independent ($iPLA_2$) and/or secreted ($sPLA_2$) isoforms of $PLA_2$. Representative $cPLA_2$ inhibitory compounds of the invention include related 2-oxoamide analogues AX006 and AX059, as described below. In contrast, a compound like AX115 has inhibitory activity for $sPLA_2$ as well as for $cPLA_2$ and $iPLA_2$. In this respect, "selectively inhibitory" refers to inhibition of the target $PLA_2$ enzyme(s) without statistically significant effect on the non-target enzymes.

More particularly, in one aspect of the invention, compounds are provided having the general structure A or isomers, enantiomeric forms, pharmacologically acceptable salts, or prodrugs thereof:

A

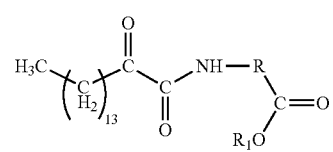

wherein R is selected from a linear or branched alkylene group, and $R_1$ is selected from a group consisting of hydrogen and methyl.

An example of the compound of structure A is the compound of formula I shown below (methyl-[(2-oxohexadecanoyl)amino)]acetate), and includes isomers, enantiomeric forms, pharmacologically acceptable salts, or prodrugs thereof. This compound, which inhibits $sPLA_2$ as well as $cPLA_2$ and $iPLA_2$, is also referred to herein as compound AX115:

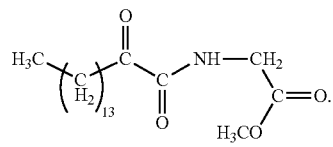

Another compound of structure A is one having the formula II shown below (4-(2-oxohexadecanoyl)amino butyric acid), and includes isomers, enantiomeric forms, pharmacologically acceptable salts, or prodrugs thereof. It is selectively inhibitory for $cPLA_2$ and is also referred to herein as compound AX006:

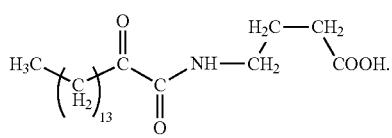

Another compound of structure A is one having the formula III shown below (4-(2-oxohexadecanoyl)amino-6-methylheptanoic acid), and includes isomers, enantiomeric forms, pharmacologically acceptable salts, or prodrugs thereof. It is selectively inhibitory for $cPLA_2$ also referred to herein as compound AX059:

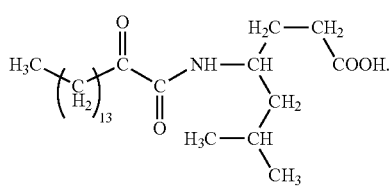

Pharmaceutical composition for use in inhibiting the enzymatic activity of target $PLA_2$ enzymes in a cell or organism, comprising a compound of any one of claims 1-5, and a pharmaceutically acceptable carrier therefor, are also provided.

BRIEF DESCRIPTION OF FIGURES

FIG. 1 is an illustration of expression of $sPLA_2$ GIIA after SCI.

FIG. 2 illustrates quantification of the changes in mRNA and protein after SCI.

DETAILED DESCRIPTION

Figure 3:
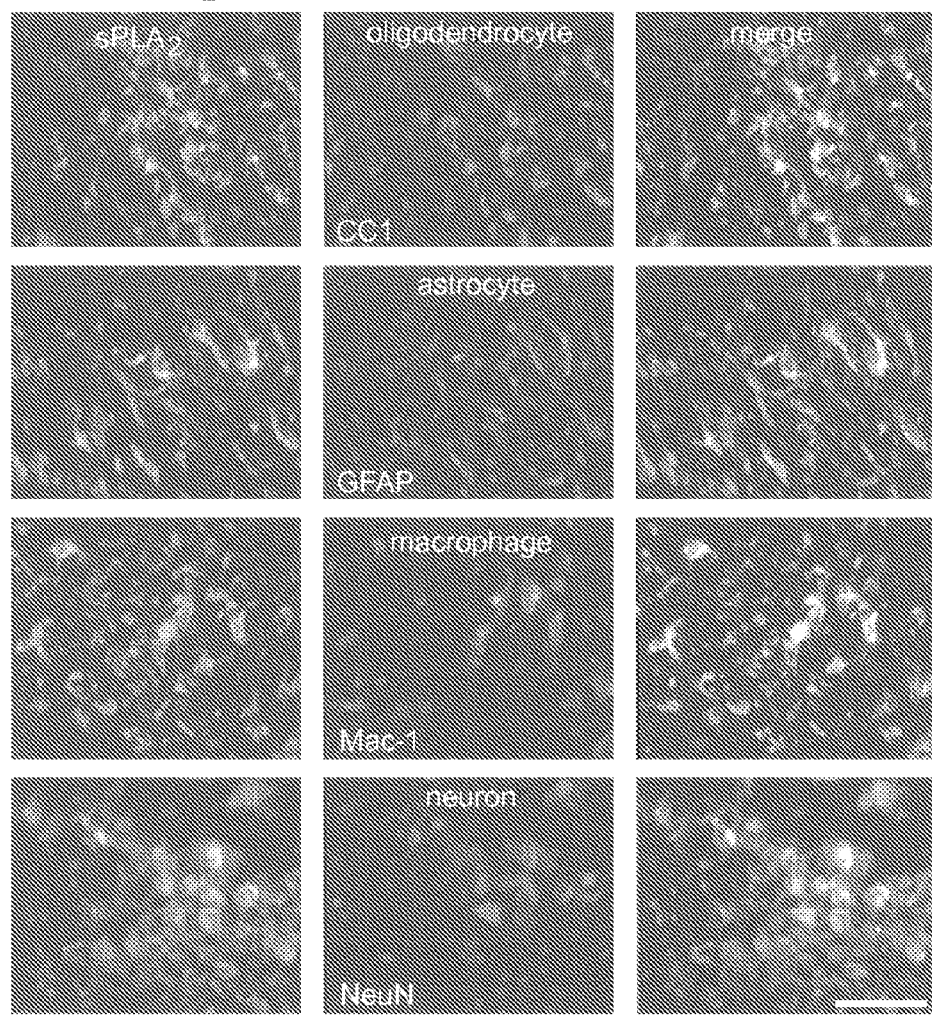
FIG. 3 is an illustration of expression of $sPLA_2$ GIIA after spinal cord contusion.

The contents of co-pending, co-owned U.S. Utility patent application Ser. No. 10/506,059, filed on Mar. 7, 2003, and of co-pending, co-owned International Patent Application No. PCT/US2006/032412 are incorporated herein by this reference. The invention is further described in detail below, and by the drawings appended hereto.

All patents and other references cited in the specification are indicative of the level of skill of those skilled in the art to which the invention pertains, and are incorporated by reference in their entireties, including any tables and figures, to the same extent as if each reference had been incorporated by reference in its entirety individually.

One skilled in the art would readily appreciate that the present invention is well adapted to obtain the ends and advantages mentioned, as well as those inherent therein. The methods, variances, and compositions described herein as presently representative of preferred embodiments are exemplary and are not intended as limitations on the scope of the invention. Changes therein and other uses will occur to those skilled in the art, which are encompassed within the spirit of the invention, are defined by the scope of the claims.

Definitions provided herein are not intended to be limiting from the meaning commonly understood by one of skill in the art unless indicated otherwise.

A. Overview of Structures of Compounds of the Invention

Compounds of the invention are constructed based on a 2-oxoamide with a hydrocarbon tail and carbon tether. An important consideration in the functionality of these agents is their high c Log P values, in the range of 6-8. It is widely considered that agents with log P values greater than 5 may not be "druggable" (Lipinski et al., *Adv. Drug Deliv. Rev.*, 46:3-26, 2001). It is important to note that in the present systems, the target of drug action is within the cytosol. This requires that the molecule have a lipophilicity that allows it to readily cross the cell membrane to interact with $PLA_2$.

AX006 and AX059 exemplify compounds with cPLA$_2$ inhibitory activity believed to be useful in the treatment of multiple sclerosis (MS) based on their potent activity in treating EAE in an animal model of MS. AX115 is an exemplary compound with sPLA$_2$ inhibitory activity (and some iPLA$_2$ and cPLA$_2$ inhibitory activity as well), which is believed to be useful in treating SCI, with functional recovery, based on the results achieved in an animal model as described herein.

B. Synthesis and Structure of PLA$_2$ Inhibitors of the Invention

The compounds of the invention are structurally designed based on the principle that the inhibitor should consist of two components: (a) an electrophilic group that is able to react with the active-site serine residue, and (b) a lipophilic segment that contains chemical motifs necessary for both specific interactions and a proper orientation in the substrate binding cleft of the enzyme (Kokotos, *J. Mol. Catal. B-Enzym.* 2003, 22:255-269). Accordingly, the invention provides a novel class of oxoamides that selectively inhibit PLA$_2$ enzymes. The oxoamides of the invention share a generic structure as shown below:

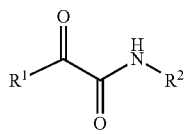

For these studies, AX006 was prepared as previously described (Kokotos, et al., supra, 2002; Kokotos et al., supra, 2004, the contents of which are incorporated herein by this reference). One synthetic scheme (also applicable to production of AX059) that may be employed to illustrate the process is as follows (synthetic Scheme 1):

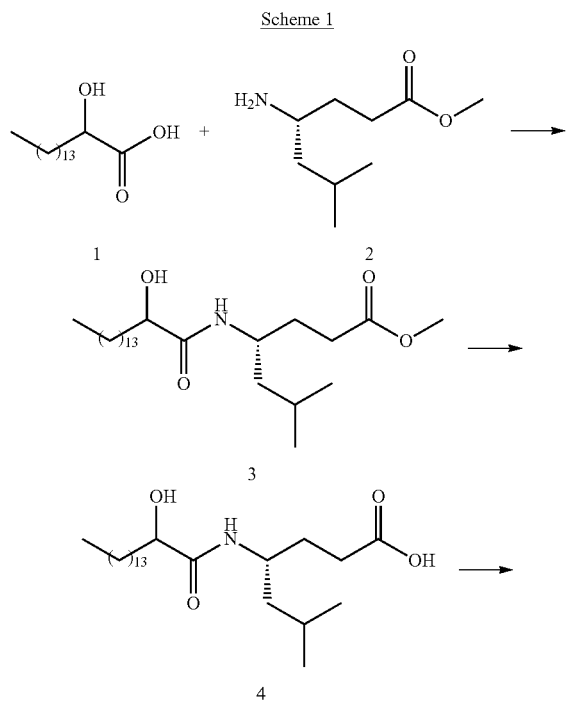

Scheme 1

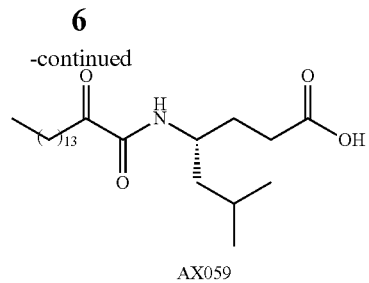

AX059

The synthetic procedure was as follows. First, a first intermediate compound, i.e., (4R)-methyl 4-[(2-hydroxyhexadecanoyl)amino]-6-methylheptanoate (3 on the synthetic Scheme 1) was obtained.

To a stirred solution of 2-hydroxy-hexadecanoic acid (540 mg, 2.0 mmol) and (R)-methyl 4-amino-6-methylheptanoate hydrochloride (419.4 mg, 2.0 mmol) in CH$_2$Cl$_2$ (20 mL), Et$_3$N (6.2 mL, 4.4 mmol) and subsequently WSCI (420 g, 2.2 mmol) and HOBt (320 mg, 2.0 mmol) were added at 0° C. The reaction mixture was stirred for 1 h at 0° C. and overnight at room temperature. The solvent was evaporated under reduced pressure, and EtOAc (20 mL) was added. The organic layer was washed consecutively with brine, 1 N HCl, brine, 5% NaHCO$_3$, and brine, dried over Na$_2$SO$_4$, and evaporated under reduced pressure. The residue was purified by column chromatography using CHCl$_3$ as the eluent.

Yield 57%; white solid; mp 37-38° C.; $^1$H NMR δ 6.30 (1H, t, J=10.8 Hz, NH), 4.07 (2H, m, 2×CH), 3.66 (3H, s, OCH$_3$), 3.04 (1H, m, OH), 2.36 (2H, t, J=7.4 Hz, CH$_2$COO), 1.95-1.50 (5H, m, 2×CH$_2$, CH), 1.40-1.18 (26H, m, 13×CH$_2$), 0.95-0.81 (9H, m, 3×CH$_3$).

Next, a second intermediate product, i.e., (4R)-4-[(2-hydroxyhexadecanoyl)amino]-6-methyl heptanoic acid (4 on the synthetic Scheme 1) was obtained.

To a stirred solution of (4R)-methyl 4-[(2-hydroxyhexadecanoyl)amino]-6-methylheptanoate (855 mg, 2.00 mmol) in a mixture of dioxane-H$_2$O (9:1, 20 mL), 1 N NaOH (2.2 mL, 2.2 mmol) was added, and the mixture was stirred for 12 h at room temperature. The organic solvent was evaporated under reduced pressure, and H$_2$O (10 mL) was added. The aqueous layer was washed with EtOAc, acidified with 1 N HCl, and extracted with EtOAc (3×12 mL). The combined organic layers were washed with brine, dried over Na$_2$SO$_4$, and evaporated under reduced pressure. The residue was purified after recrystallization [EtOAc-petroleum ether (bp 40-60° C.)].

Yield 65%; white solid; mp 73-74° C.; $^1$H NMR δ 6.50 (1H, m, NH), 4.05 (2H, m, 2×CH), 2.40 (2H, m, CH$_2$COO), 2.00-1.50 (5H, m, 2×CH$_2$, CH), 1.40-1.18 (26H, m, 12×CH$_2$), 0.95-0.81 (9H, m, 3×CH$_3$).

Finally, the final product, i.e., compound AX059 was obtained. To a solution of (4R)-4-[(2-hydroxyhexadecanoyl) amino]-6-methylheptanoic acid (827.2 mg, 2.00 mmol) in a mixture of toluene-EtOAc (1:1, 12 mL), a solution of NaBr (0.22 g, 2.1 mmol) in H$_2$O (1 mL) was added, followed by AcNH-TEMPO (4 mg, 0.02 mmol). To the resulting biphasic system, which was cooled to 0° C., an aqueous solution of 0.35 M NaOCl (6.2 mL, 2.2 mmol), containing NaHCO$_3$ (0.50 g, 6 mmol), was added dropwise with vigorous stirring at 0° C. over 1 h. The mixture was stirred for 15 min at 0° C., and H$_2$O (4 mL) was added. The aqueous layer was separated, acidified with 1 N HCl, and extracted with EtOAc (2×12 mL). The combined organic layers were washed consecutively with 5% aqueous KI (12 mL), 10% aqueous Na$_2$S$_2$O$_3$ (12 mL), and brine, dried over Na$_2$SO$_4$, and evaporated under reduced pressure. The residue was purified by column chromatography using EtOAc as the eluent.

Yield 70%; white solid; mp 65-66° C.; $[\alpha]_D$-14.0 (c 1.0, $CH_3Cl$); $^1H$ NMR δ 6.81 (1H, d, J=9.6 Hz, NH), 4.03 (1H, m, CH), 2.93 (2H, t, J=7.0 Hz, $CH_2COCO$), 2.37 (2H, m, J=7.0 Hz, $CH_2COOH$), 1.91 [3H, m, $CH_2$, $CH(CH_3)_2$], 1.59 (4H, m, 2×$CH_2$), 1.25 (22H, m, 11×$CH_2$), 0.89 (9H, t, J=6.8 Hz, 3×$CH_3$); $^{13}C$ NMR δ 199.4, 178.6, 160.1, 47.4, 44.3, 36.8, 31.9, 30.7, 30.4, 29.6, 29.4, 29.3, 29.0, 24.8, 23.2, 23.0, 22.7, 22.0, 14.1.

Methyl-[(2-oxohexadecanoyl)amino)]acetate also described as methyl 2-(2-oxohexadecaneamido)acetate (AX115) was synthesized as shown by the synthetic Scheme 2:

Scheme 2

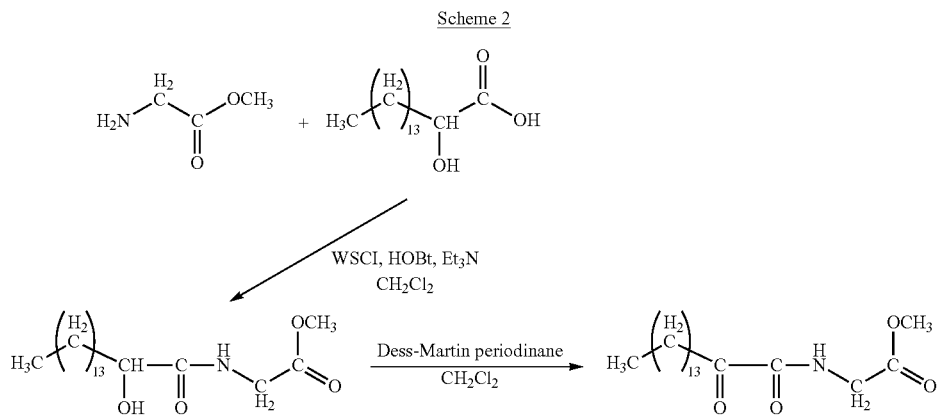

As shown on the synthetic Scheme 2, aminomethyl acetate was coupled with 2-hydroxy-hexadecanoic acid using 1-(3-dimethylaminopropyl)-3-ethyl carbodiimide (WSCI) as a condensing agent in the presence of 1-hydroxybenzotriazole (HOBt). The resulting 2-hydroxyamide was oxidized by treatment with Dess-Martin reagent to obtain the final product, i.e., compound AX115.

More specifically, to a stirred solution of 2-hydroxy-hexadecanoic acid (1.0 mmol) and aminomethyl acetate (in hydrochloride form) (1.0 mmol) in $CH_2Cl_2$ (10 mL), $Et_3N$ (3.1 mL, 2.2 mmol) and subsequently WSCI (0.21 g, 1.1 mmol) and 1 HOBt (0.14 g, 1.0 mmol) were added at 0° C. The reaction mixture was stirred for 1 hour at 0° C. and overnight at room temperature. The solvent was evaporated under reduced pressure and EtOAc (20 mL) was added. The organic layer was washed consecutively with brine, 1N HCl, brine, 5% $NaHCO_3$, and brine, dried over $Na_2SO_4$ and evaporated under reduced pressure. The residue was purified by column-chromatography using $CHCl_3$/MeOH as eluent.

The resulting product was then oxidized. To a solution of 2-hydroxy-amide (1 mmol) in dry $CH_2Cl_2$ (10 mL) Dess-Martin periodinane was added (0.64 gr, 1.5 mmol) and the mixture was stirred for 1 hour at room temperature. The organic solution was washed with 10% aqueous $NaHCO_3$, dried over $Na_2SO_4$ and the organic solvent was evaporated under reduced pressure. The residue was purified by column-chromatography using $CHCl_3$ as eluent, to yield the final product, i.e., compound AX115, as a white solid.

Yield 91%; m.p. 79-81° C.; $^1H$ NMR δ 7.40 (1H, m, COCONH), 4.09 (2H, d, J=5.8 Hz, $CH_2NH$), 3.79 (3H, s, $COOCH_3$), 2.91 (2H, t, J=7.8 Hz, $CH_2COCO$), 1.61 (2H, m, $CH_2$), 1.25 (22H, br s, 11×$CH_2$), 0.88 (3H, t, J=6.6 Hz, $CH_3$); $^{13}C$ NMR δ 198.2, 169.3, 160.2, 52.5, 40.9, 36.7, 31.9, 29.62, 29.56, 29.4, 29.33, 29.30, 29.0, 23.1, 22.7, 14.1; MS (ESI): m/z (%): 288 (100), 364 (51) $[M+Na]^+$. $C_{19}H_{35}NO_4$ (M.W.=341.49): Calc.: C, 66.83; H, 10.33; N, 4.10. Found: C, 66.92; H, 10.25; N, 4.04.

C. GIVA and GVIA $PLA_2$ Selective Inhibition by Inhibitors of the Invention.

The compounds described herein were tested for inhibition of $PLA_2$s in in vitro assay systems. The data, summarized in the Examples, are represented as $X_f(50)$ values unless otherwise noted. $X_f(50)$ is defined as the inhibitor concentration that produced 50% inhibition. $X_f(50)$ is used as opposed to the more common $IC_{50}$ because GIVA and GVIA $PLA_2$ are active at a two-dimensional lipid interface rather than in three-dimensional solution. (Deems, *Anal. Biochem.*, 287:1-16, 2000).

1. Inhibition of $sPLA_2$ and $iPLA_2$ and $cPLA_2$ in Treatment of SCI.

Oligodendrocyte apoptosis is known to occur after SCI. Lysophosphatidylcholine (LPC) can be generated in apoptotic cells by the actions of the low molecular weight form (52 kDa) of $iPLA_2$. This $iPLA_2$ generated LPC acts as a chemoattractant for macrophages that would then phagocytose damaged cells. In addition to phosphatidylserine displayed on the surface of dying cells which acts as an "eat me" signal for macrophages, C-reactive protein, which can activate the classic complement pathway, has a high affinity for lysophospholipids, particularly LPC, and could therefore trigger the axonal and myelin damage.

In an animal (mouse) model of SCI (contusion injury-induced lesions of the spinal cord) as described more fully in Example 2, $iPLA_2$ mRNA is increased by ~2-fold at day 14 following SCI; e.g., quantification of the protein expression detected by Western blotting showed a 3.2-fold increase at day 14. At days 7 and 14, $iPLA_2$ immunostaining was also localized to axonal membranes of myelinated and unmyelinated axons. Increased $iPLA_2$ activity at these sites might cause selective damage of axonal membranes and lead to axonal degeneration after SCI.

FIGS. 1 and 2 illustrate $sPLA_2$ mRNA expression. Expression of $sPLA_2$ GIIA is increased after SCI, i.e., $sPLA_2$ GIIA mRNA expression is increased from 1 to 28 days after SCI as detected by RT-PCR (FIG. 1a), and $sPLA_2$ GIIA protein expression is increased after SCI as detected by Western blot (FIG. 1b). FIG. 1c shows the results where RT-PCR for peptidylprolyl isomerase A (PPIA) was used as control and FIG. 1d shows Western blot for β-actin used as loading control.

FIG. 2 demonstrates quantification of the changes in mRNA levels of sPLA$_2$ GIIA from 1 to 28 days after SCI by RT-PCR (FIG. 2a), and quantification of sPLA$_2$ group GIIA protein levels from 1 to 28 after SCI assessed by Western blot (FIG. 2b). As can be seen from FIG. 2, sPLA$_2$ GLIA is significantly up-regulated at 3 and 7 days after SCI. Although sPLA$_2$ GIIA antibodies may cross react with sPLA$_2$ GV, the lack of sPLA$_2$ GV mRNA in the spinal cord after SCI suggests that the band observed in the Western blots for sPLA$_2$ GIIA is specific for this particular PLA$_2$ form.

As can be further seen, sPLA$_2$ mRNA expression also increased rapidly after SCI reaching ~100-fold by day 28 following SCI. Quantification of protein expression by Western blotting showed ~35-40 fold increase at days 3 and 7 (FIG. 2b). Many sPLA$_2$ immunoreactive cells were seen in white and grey matter at days 3 and 7.

FIG. 3 shows double immunofluorescence images of sPLA$_2$ GIIA (green) co-labeled with anti-CC-1 (oligodendrocytes), anti GFAP (astrocytes), anti Mac-1 (macroglia/macrophages), and NeuN antibody (neurons). sPLA$_2$ GIIA is mainly expressed in astrocytes and oligodendrocytes, although some microglia/macrophages and neurons also express it. Bar=50 μm.

As can be seen from FIG. 3, in the grey matter, GIIA was mainly expressed in astrocytes, some neurons and Mac-1$^+$ macrophages/microglia. As with iPLA$_2$, sPLA$_2$ was also expressed mainly in oligodendrocytes (FIG. 3) and some astrocytes and Mac 1$^+$ cells in the white matter.

Next assessed was the role of cPLA$_2$, iPLA$_2$, and sPLA$_2$ after SCI using compounds of the instant invention (Table 1). An animal model of spinal cord injury (SCI) described in Example 2 was treated as described in Example 3.

Figure 4A:
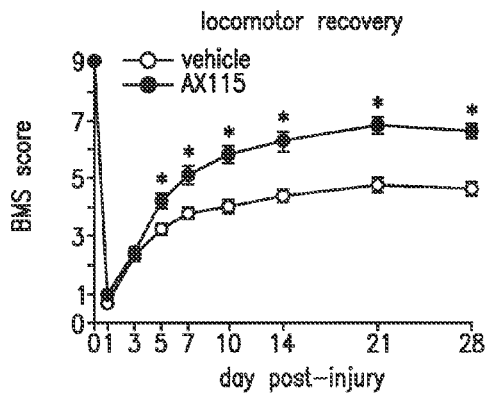
FIG. 4 is an illustration of locomotor recovery after SCI.
Figure 4B:
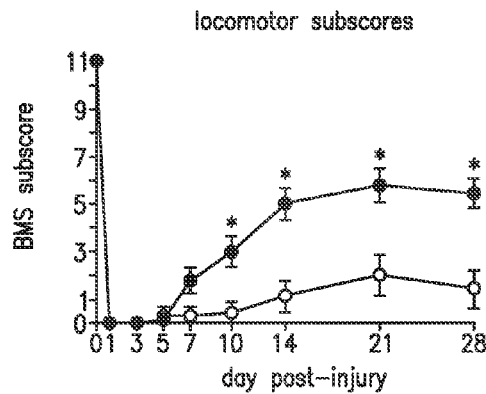

The data on locomotor recovery in mice treated with the compounds of Table 1 are shown in FIG. 4. FIG. 4a includes charts showing time course of locomotor recovery evaluated by the BMS scores. Treatment with AX115 shows marked improvement in the BMS scores starting from 5 days after SCI. FIG. 4b demonstrates that AX115 treated mice also display a marked improvement in the finer aspects of locomotor control showing an increase of 4 points in the BMS subscores (*p<0.05).

Daily administration of AX115 started 1 hour after injury markedly improved locomotor function as compared to vehicle treated injured mice. Post-hoc analysis revealed significant improvements in BMS scores beginning at 5 dpi, which remained significantly elevated for the duration of the experiment (FIG. 4a). By 28 days, the vehicle treated mice were able to step occasionally or frequently but without co-ordination or proper paw placement (score 4.6). In contrast, the AX115 treated mice displayed stepping with frequent co-ordination with proper placement of the paws (score 6.6). In addition, fine locomotor control evaluated by the BMS subscores showed a 4-point improvement with sPLA$_2$ inhibitor treatment (FIG. 4b).

Some results of treatment using the inhibitor AX115 are provided on FIGS. 5 and 6. FIG. 5a demonstrates that AX115 treated animals show significant amount of tissue sparing at the lesion epicenter and adjacent regions (*p<0.01). FIG. 5b demonstrates that Mice treated with AX115 have significantly greater neuron survival in regions ranging from 300 to 1000 μm rostral and caudal to the lesion epicenter {*p<0.05). FIG. 5c demonstrates that mice treated with AX115 show a marked reduction of myelin loss in the epicenter and 300 μm rostral and caudal to the lesion site (*p<0.01). Finally, FIG. 5d demonstrates that animals treated with AX115 display significantly greater serotonergic innervation 1000 μm caudal to the lesion epicenter (*p<0.05).

FIG. 6 demonstrates effects of AX115 on animals after SCI. FIGS. 6a and 6b include representative micrographs showing GFAP staining at the epicenter of the injury taken from mice treated with vehicle (FIG. 6a), and AX115 (FIG. 6b) at 28 dpi. Note a marked reduction in tissue loss (outlined by dashed lines) in mice treated with AX115 as compared to the vehicle treated injured controls. FIGS. 6s and 6d include micrographs showing cresyl-violet stained ventral horn regions of the spinal cord 500 μm caudal to the epicentre from mice treated with vehicle (FIG. 6c) and AX115 (FIG. 6d).

TABLE 1

| Inhibitor | Structure | cPLA$_2$GIVA | iPLA$_2$GIVA | sPLA$_2$ GIVA/GV* |
|---|---|---|---|---|
| | | Inhibition (at 0.091 mol fraction) | | |
| AX059 | (structure shown) | >95 X$_1$(50) = 0.008 ± 0.002 | 0 | 0 |
| AX115 | (structure shown) | 62% | 45% | 52% |

Figure 6A:
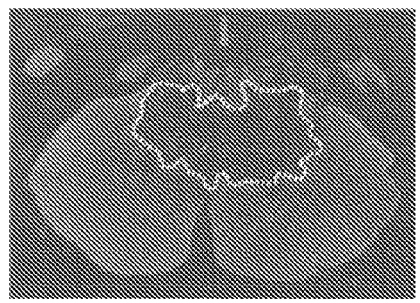
FIG. 6 is an illustration of effects of AX115 after SCI.
Figure 6B:
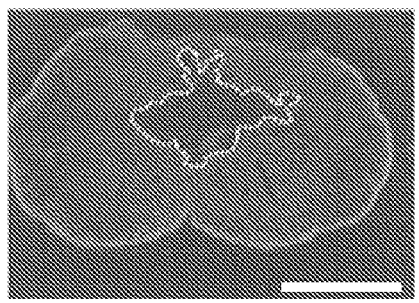
Figure 6C:
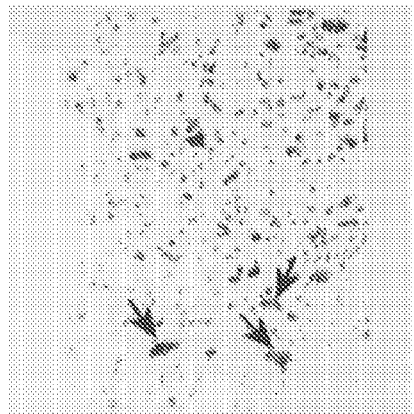
Figure 6D:
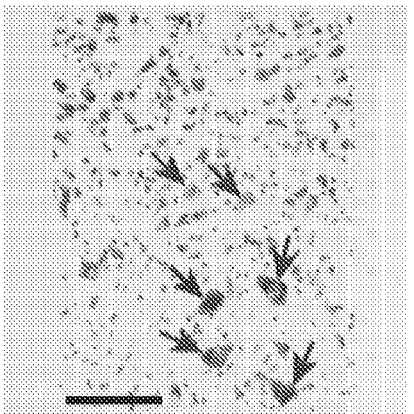
Figure 6E:
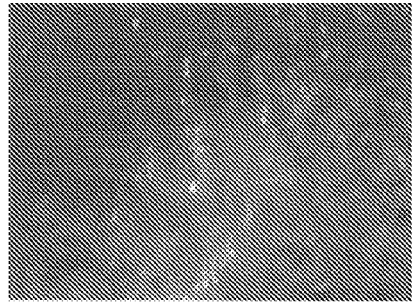
Figure 6F:
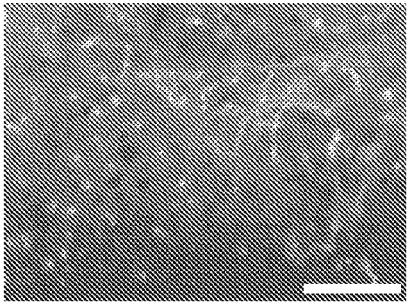
Figure 6G:
Figure 6H:
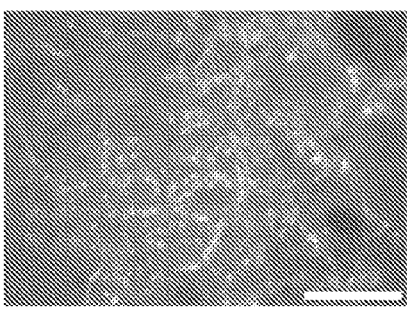

Note the greater number of neuronal profiles (arrows) in mice treated with AX115 as compared to the vehicle treated control. FIGS. 6e-6h include micrographs showing 5-HT immunoreactive fibers in the lateral funiculi (FIGS. 6e, 6f) and ventral horn (FIGS. 6g, 6h) taken from a distance of 1000 μm caudal to the lesion site in animals treated with vehicle (FIGS. 6e, 6g) and AX115 (FIGS. 6f, 6h). A marked increase of serotonergic fibers is seen in the lateral funiculi and ventral horns of mice treated with AX115 as compared to vehicle treated injury controls. Scale bar=500 μl in a, b; =50 μm in c-h.

Figure 5A:
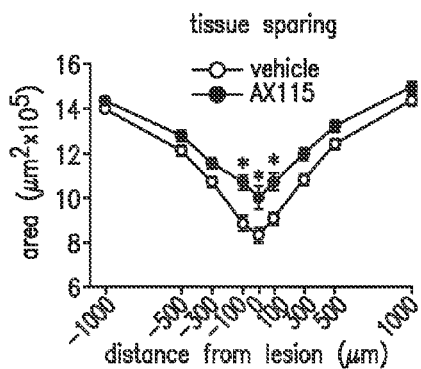
FIG. 5 is an illustration of the results of treatment using compound AX115.
Figure 5B:
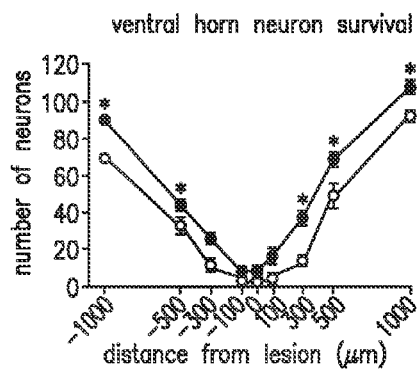
Figure 5C:
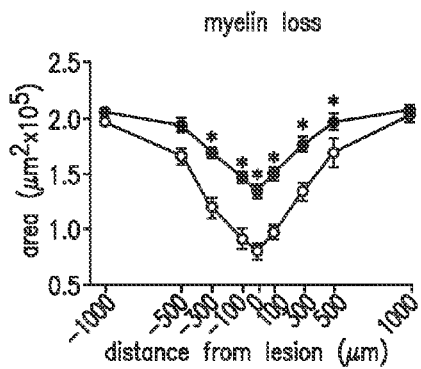
Figure 5D:
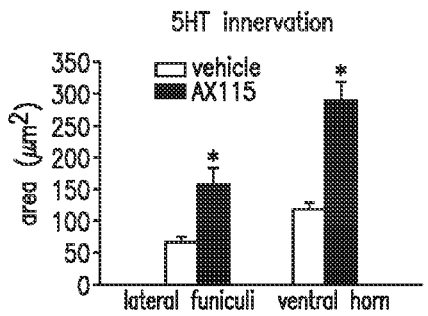

Accordingly, treatment with the inhibitor AX115 promoted: (i) significant tissue protection (FIGS. 5a and 6b) and myelin sparing (FIG. 5c) at the lesion epicentre and adjacent areas; (ii) a 3-fold increase in the density of 5-HT fibers within the lateral funiculi and ventral horns (FIGS. 5d and 6f, h); and (iii) significantly better survival of ventral horn neurons for distances of up to 1 mm rostral and caudal to the lesion (FIGS. 5b and 6d). These data clearly demonstrate an important role of sPLA$_2$ in the evolution of the secondary pathology after SCI. sPLA$_2$ secreted by glial cells can degrade myelin because phosphatidylcholine is preferentially located on the outer side of the myelin membranes. LPC produced by the actions of sPLA$_2$ is also a potent demyelinating agent and at higher levels may cause axonal and neuronal damage. This is supported by the greater protection of 5HT axons and myelin, and the improved neuronal survival seen after SCI in mice treated with the sPLA$_2$ inhibitor.

Figure 7A:
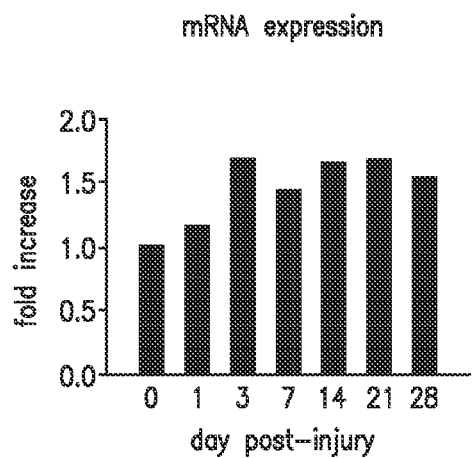
FIG. 7 is an illustration of the changes of GIVA $cPLA_2$ as correlated with measures of disease.
Figure 7B:
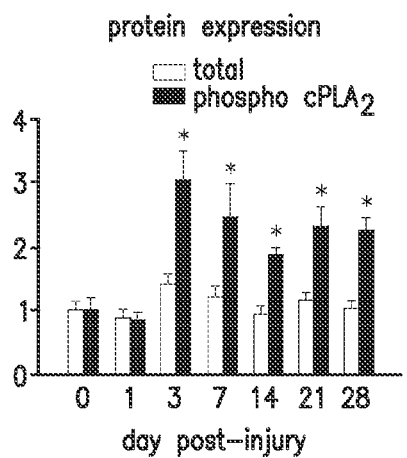

As shown in FIG. 7, the fact that AX115 does not substantially inhibit the activity of cPLA$_2$ has surprising therapeutic benefits in treatment of SCI. cPLA$_2$ mRNA is constitutively expressed in the uninjured spinal cord and is up-regulated about 2-fold at 3 days after SCI, and remained elevated until day 28 (FIG. 7a). The total cPLA$_2$ protein, however, remains unchanged (FIG. 7b). Double immunofluorescence labeling with cell type-specific antibodies revealed that at 3 dpi cPLA$_2$ is expressed in neurons and some oligodendrocytes located in areas adjacent to the lesion epicentre (FIG. 7c). It was, however, not expressed in macrophages/microglia or astrocytes.

As described more fully in Examples 13 and 14, the functional role of cPLA$_2$ in SCI was assessed by comparing the effects of contusion injury in cPLA$_2^{-/-}$ mice and cPLA$_2^{+/+}$ littermates. Surprisingly, locomotor recovery assessed using the 9-point Basso Mouse Scale (BMS) was worse in cPLA$_2^{-/-}$ mice compared to wildtype mice (FIG. 7d-e). Histological analyses also revealed greater tissue and neuronal loss in cPLA$_2^{-/-}$ as compared to cPLA$_2^{+/+}$ mice. cPLA$_2$-deficient mice showed: (i) significant reduction in tissue sparing (FIG. 7f); (ii) significant reduction in the number of surviving ventral neurons (FIG. 7g); (iii) significantly greater myelin loss in areas adjacent to the lesion epicentre (FIG. 7h); and (iv) tissue cavitation, an unusual feature in mice with SCI. Thus, contrary to other models of CNS inflammation in which cPLA$_2$ has been shown to induce inflammation and tissue damage including ischemic injury in the cerebral cortex, the present data indicates that cPLA$_2$ has a protective role after SCI. cPLA$_2$ was also shown to be required for the survival of cortical and hippocampal neurons in vitro, and recent work indicates that cPLA$_2$ promotes survival of human embryonic kidney cells after calcium overexposure by prostaglandin-mediated mechanisms.

Figure 8:
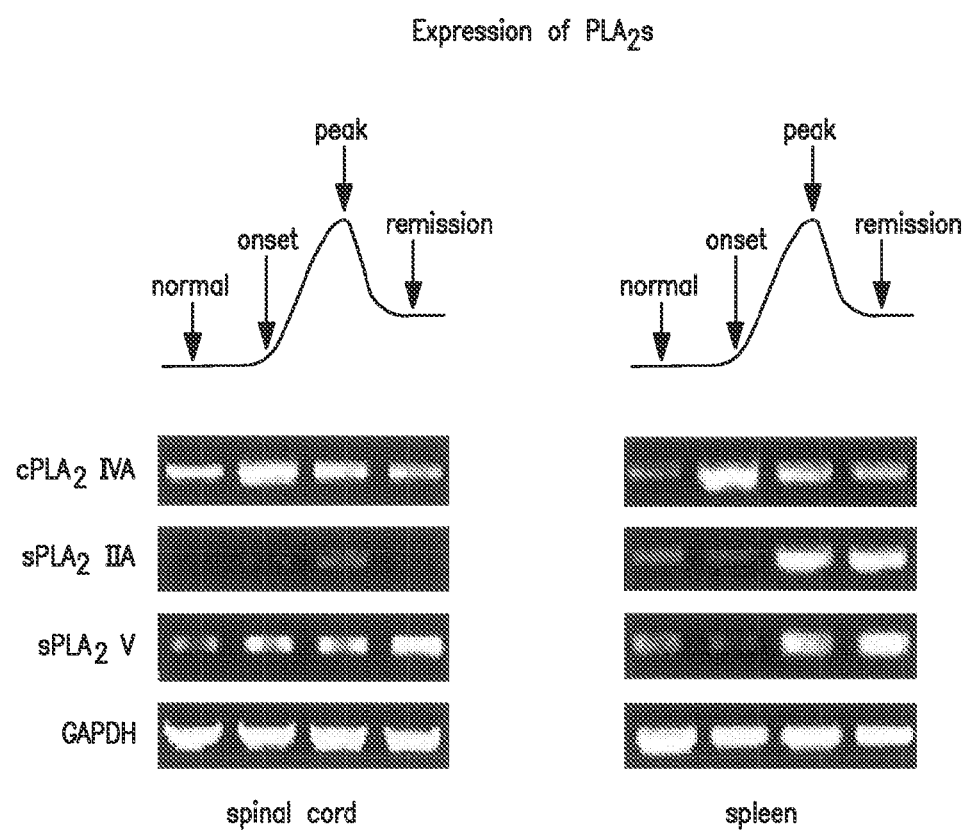
FIG. 8 is an illustration of the results of RT-PCR analysis of mRNA expression of some members of the $PLA_2$ family in the spinal cord and spleen of normal mice and EAE mice.
Figure 9:
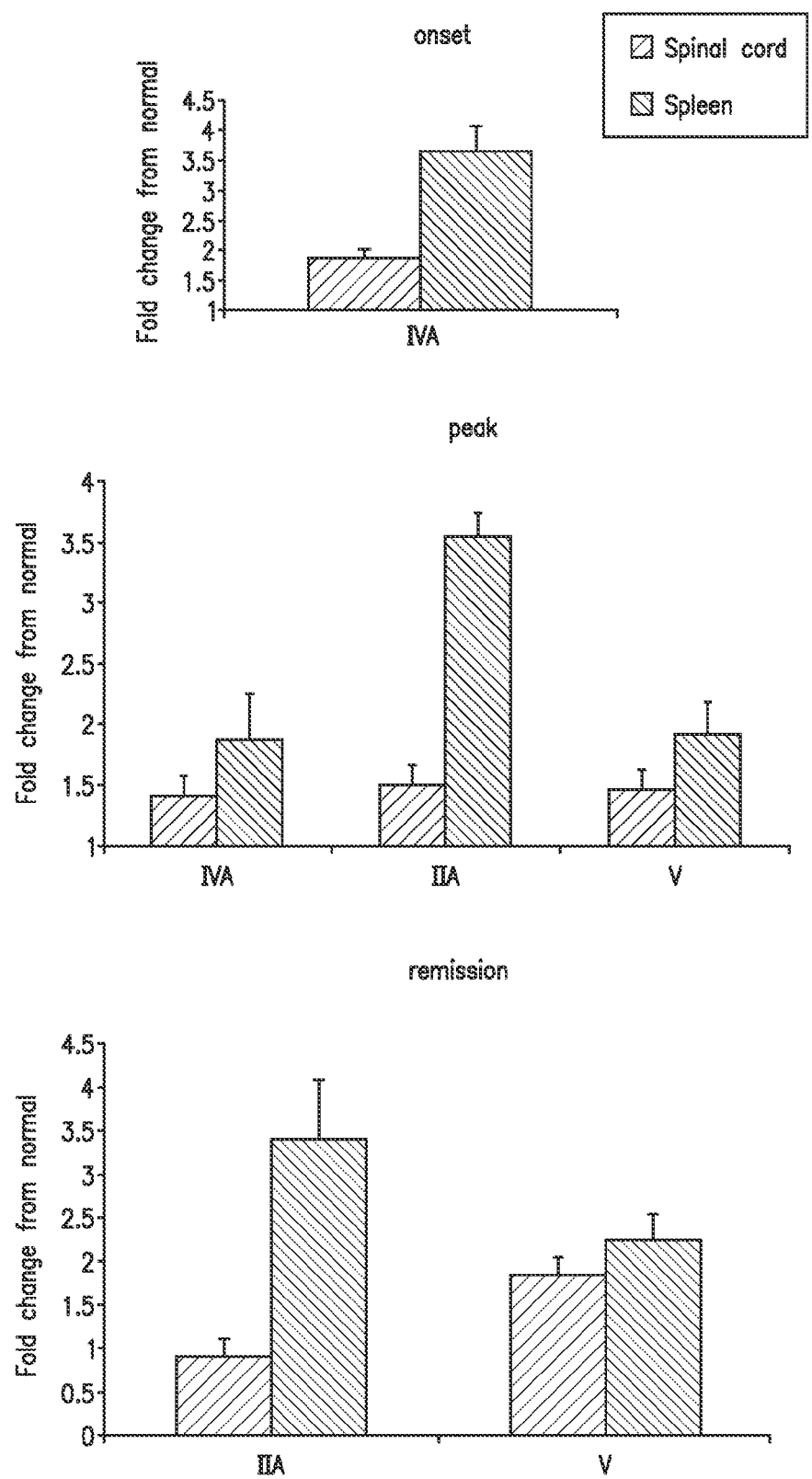
FIG. 9 is an illustration of various stages of disease in SJL/J mice.

FIG. 8 is an illustration of the results of RT-PCR analysis of mRNA expression of some members of the PLA$_2$ family in the spinal cord and spleen of normal mice and EAE mice. FIG. 8 illustrates the results of RT-PCR analysis of mRNA expression of 4 members of the PLA$_2$ family in the spinal cord and spleen of normal mice, and EAE mice at the onset, peak and remission stages. cPLA$_2$ group VA is highest at the onset in the spinal cord and spleen. It then decreases at the peak and further in the remission stages. sPLA$_2$ group IIA is increased slightly at the peak stage in the spinal cord but is markedly increased in the spleen at the peak and remission. sPLA$_2$ group V is highest at the remission stage in the spinal cord and spleen. These data represent 3 animals tested per group. FIG. 9 is an illustration of various stages of disease in SJL/J mice.

Blocking enzymes downstream of PLA$_2$, such as COX-2 or 5-lipoxygenase, ameliorates only some of the detrimental effects of SCI. PLA$_2$ enzymes are therefore much better targets for therapeutic intervention. These results show the need to selectively target those PLA$_2$s that are detrimental (e.g., sPLA$_2$) in SCI while not altering others that are beneficial (cPLA$_2$). The inhibitor treatment is effective when initiated one hour after SCI, making this a therapeutically viable approach. Inhibitors such as the AX115, or related compounds, are likely to be excellent and selective agents for the treatment of acute SCI.

2. Use of PLA$_2$ Inhibitors to Treat Multiple Sclerosis.

Multiple sclerosis (MS) is an autoimmune demyelinating disease of the central nervous system (CNS) that affects over a million people worldwide. The disease onset is generally between the second and third decades of life, with increasing cases of juvenile disease being reported. MS affects women more often than men. As MS is characterized by focal inflammatory lesions that can occur in any region of the CNS, the symptoms are varied and include motor paralysis, sensory loss or paresthesias, and bowel and bladder dysfunction. Although the cause of MS is still not fully known, genetic and environmental factors increase susceptibility to the disease. Experimental autoimmune encephalomyelitis (EAE) is widely used as an animal model of MS. EAE has provided important insights into the onset and progression of CNS demyelinating autoimmune disease. In the EAE model in which mice are actively immunized with myelin antigens mixed with adjuvant T cells become activated in the periphery to a Th1 phenotype (as reflected for example in interferon-y (IFN-y) and IL-2 expression), then migrate to the CNS where the myelin-reactive T cells become reactivated by antigen presenting cells. The reactivated Th1 T cells induce the further recruitment of T cells and macrophages and activation of CNS glia (microglia and astrocytes), which then leads to demyelination and axonal damage. EAE shares some of the pathological features of MS and has helped to understand some of the complex immunological networks that mediate diseases.

Although the primary events that trigger MS is still unknown, the findings to date suggest that T-cells in the periphery become reactive to certain myelin antigens by as yet unknown mechanisms that eventually resulting in robust inflammatory lesions in the CNS. The exact mechanisms underlying the formation of these lesions in the CNS are not fully understood. A candidate that could serve as a mediator in evoking the pathological changes seen in the CNS in MS and EAE is the enzyme phospholipase A$_2$ (PLA$_2$). The metabolic products of PLA$_2$ can induce both inflammation and demyelination, two of the hallmarks of MS.

The AA pathway leads to the formation of leukotrienes (LT), prostaglandins (PG) and thromboxanes (TX). These lipid metabolites are collectively referred to as eicosanoids and can contribute to inflammation by chemotaxis of immune cells, by increasing vascular permeability, or by promoting the production of pro-inflammatory cytokines. LPC can also contribute to these inflammatory changes, and is also a strong myelinolytic agent. In late stages of demyelination it may also damage axonal membranes. Therefore, PLA$_2$ can set off a robust inflammatory and demyelinating response in the CNS in MS and EAE via multiple pathways.

As described more fully in Example 1, the C57BL/6 mouse strain has a naturally occurring null mutation of a major form of sPLA$_2$ group IIA. Using this mouse strain, it has previously been shown that cPLA$_2$ plays an important role in the onset and progression of EAE. In these experiments, arachidonyl-trifluoromethyketone (AACOCF$_3$), which inhibits various members of the PLA$_2$ family, was shown to markedly reduce the onset and progression of the disease. Additionally, cPLA$_2$ group IVA knockout mice on the C57BL/6 background were shown to be resistant to EAE.

To fully address the role of sPLA$_2$ (group IIA and V) and cPLA$_2$ (group IVA) in EAE. The effects of three 2-oxoamide inhibitors were assessed in the SJL/J mouse strain that expresses all forms of PLA$_2$, as described more fully in Examples 4-6. There is evidence to indicate that sPLA$_2$ may act synergistically with cPLA2, in a positive feedback mechanism or under other conditions they may interact by negative-feed back way. As shown herein, sPLA$_2$ and cPLA$_2$ have opposite roles in influencing the progression of the disease.

The results disclosed herein indicate that the expression of cPLA$_2$ group IVA and sPLA$_2$ group IIA and V are increased in different stages of EAE in SJL/J mice. cPLA$_2$ group IVA levels increase at the onset of the disease while sPLA$_2$ IIA and V levels increase at the peak and remission stages. Previous work has showed that the broader cPLA$_2$ family plays a role in the onset and progression of EAE in the C57BL/6 strain of mice. Using more specific inhibitors to cPLA$_2$ group IVA (AX006 and AX059) it is demonstrated herein that cPLA$_2$ group IVA plays a role in the initiation of EAE. These 2-oxoamide inhibitors reduce the severity of the disease during the period that they were administered. It is possible that continued administration might prevent later clinical attacks. sPLA$_2$ on the other hand appears to serve a protective role in EAE by contributing to the establishment of remission. These experiments point to the importance of selective blocking of PLA$_2$ for the treatment of MS.

The following examples are intended to further illustrate but not limit the scope of the invention.

EXAMPLE 1

General Experimental Procedures—Materials and Methods, MS Animal Model

Generation of EAE

EAE was induced in female SJL/J mice by subcutaneous injections of 100 μg of proteolipid protein (PLP) (Sheldon Biotechnology Centre, Montreal, Canada) in Complete Freund's Adjuvant (CFA) [Incomplete Freund's adjuvant containing 4 mg/ml of heat inactivated *Mycobacterium tuberculosis* (Fisher Scientific, Nepean, Canada)]. Mice were boosted on day 7 with 50 μg of PLP in CFA containing 2 mg/ml of heat inactivated *Mycobacterium tuberculosis*. The mice were monitored daily for clinical symptoms of EAE using the following 5-point scale: Grade 0=normal (no clinical signs), Grade 0.5=partial flaccid tail, Grade 1=complete flaccid tail, Grade 2=mild hindlimb weakness (fast righting reflex), Grade 3=severe hindlimb weakness (slow righting reflex), Grade 4=hindlimb paralysis, Grade 5=hindlimb paralysis and forelimb weakness or moribund. The person doing the clinical monitoring was blind to the experimental groups.

RT-PCR

Spinal cords and spleens were removed from animals at the onset, peak, and remission stages of disease, and RNA isolated using the RiboPure™ kit (Ambion Inc, Austin, Tex.) and reverse transcribed to cDNA. RT-PCR was performed using the GeneAmp RNA PCR kit (PerkinElmer Life Sciences).

Double Immunofluorescence

Mice at different clinical stages (onset, peak, remission) were deeply anesthetized and intracardially perfused with 0.1 M phosphate buffer followed by perfusion with 4% paraformaldehyde in 0.1 M phosphate buffer. Cryostat sections (12 μm) were blocked in 0.1% Triton-X 100 and 10% normal goat serum and incubated overnight with polyclonal anti-cPLA$_2$ GIVA (Santa Cruz Biotechnology, 1:75), anti-iPLA$_2$ GVIA, anti-sPLA$_2$ IIA or anti sPLA$_2$ V (Cayman Chemicals, 1:500, 1:100, 1:100, respectively) combined with monoclonal antibodies specific for astrocytes (mouse anti-GFAP, Sigma, 1:1000) or oligodendrocytes (mouse anti-APC, Calbiochem, 1:30). This was followed by incubation with a biotinylated goat anti rabbit secondary antibody (Jackson ImmunoResearch Laboratories, West Grove, Pa., 1:400) combined with a goat anti-mouse rhodamine-conjugated secondary antibody (Jackson ImmunoResearch Laboratories, West Grove, Pa., 1:200). After washing, the sections were incubated with fluorescein-conjugated streptavidin (Molecular Probes, Eugene, Oreg., 1:400).

Histochemistry and Immunohistochemistry of Postmortem MS Tissue

The tissue analyzed in this study was from archival paraffin-embedded blocks and its use for research was approved by the University of Calgary Research Ethics Board. Tissue was obtained at autopsy from three patients with MS (25 year-old male, 34 year-old female, and 38 year-old female; postmortem delay of less than 24 hours). The diagnosis of MS was confirmed by a neuropathologist. Coexisting neuropathology was excluded. The tissue blocks containing MS lesions were sampled from various CNS regions particularly the spinal cord. Each block was cut for 6 um sections, which were then used for histological and immunofluorescence analyses. The MS lesions were classified into active lesions, chronic active, and chronic inactive lesions, based on the Bo/Trapp staging system (53, 54). All the patients had active lesions and/or chronic active lesions (data not shown). Active lesions were actively demyelinating and acutely inflammatory throughout the lesion, with heavy infiltration of CD3$^+$ T cells and CD68$^+$ macrophages, as well as damaged axons immunoreactive for amyloid precursor protein; chronic active lesions were hypocellular in the cores, but hypercellular along the edges that contained focal demyelinating and inflammatory activity.

Sections were deparaffinized, rehydrated and antigen retrieval performed in sodium citrate (pH 6.0) for 20 min at 95° C. Sections were washed with PBS, placed in 2% H$_2$O$_2$ for 10 min at room temperature and blocked in 0.1% Triton-X containing 2% normal donkey serum and 1% ovalbumin. For immunohistochemistry sections were incubated overnight with rabbit polyclonal anti-iPLA$_2$ GVIA (1:200; Cayman Chemical). Sections were washed and incubated with biotinylated secondary antibody (1:400; Jackson Immunoresearch) and then incubated with Vectastain® Elite ABC kit (Sigma-Aldrich). Sections were visualised by colour reaction using 3,3-diaminobenzidine tetrahydrochloride solution (Sigma-Aldrich), counterstained with hematoxylin, dehydrated, cleared and mounted. For immunofluorescence double-labelling, sections were incubated overnight with polyclonal iPLA$_2$ GVIA combined with a rat monoclonal anti-Mac-2 (1:2, hybridoma supernatant) to identify activated macrophages. Sections were washed and visualised by incubation with Alexa 488-conjugated donkey anti-rabbit (1:400, Molecular Probes), and Alexa544-conjugated donkey anti-rat (1:400, Molecular Probes). Another series of sections were stained with Luxol fast blue and hematoxylin to identify the areas of demyelination.

Fluorescence Activated Cell Sorting (FACS)

Mice were anesthetized at the onset, peak and remission stages of disease and intracardially perfused with 20 ml of PBS. Brains and spinal cords, and spleens from 6 mice were collected and dissociated at each stage of disease, into a single-cell suspension by passing through a 70 μm pore size cell strainer (BD Biosciences). After centrifugation with 37%

Percoll (Amersham Biosciences), cells were resuspended in buffer containing mouse IgG to block nonspecific antibody binding. These cells were then stained with the following antibodies: Polyclonal rabbit anti-cPLA$_2$, anti-iPLA$_2$, anti-sPLA$_2$IIA, and anti-sPLA$_2$V; monoclonal, FITC-conjugated anti-CD4, anti-CD8, anti-Mac-1/CD11b, and anti-CD11c, (BD Pharmingen, 1:200). Goat anti-rabbit biotin and PE-conjugated strepavidin were sequentially added thereafter. Cells were isolated using a FACSVantage cell sorter (BD Immunocytometry Systems-Lyman Duff Medical Building), and flow cytometry data was analyzed using the CellQuest™ software. The FACS analysis of the different immune cell types were repeated 4 times.

Treatment of EAE-Induced Mice

EAE induced mice were randomly assigned to each of the treatment and control groups. For the groups that received treatment before the onset of clinical symptoms, treatment was started on day 5 after immunization and given daily for 3 weeks. Daily injections of the compounds AX059 and AX115 were given on a 3-day cycle consisting of one intravenous injection (100 μl) followed by 2 intraperitoneal injections (200 μl) of a 2 mM solution. Mice in the control group were treated with the vehicle used to suspend the inhibitors, i.e., PBS containing 5% Tween 80.

For the groups that received delayed treatment after symptoms occurred, mice were treated with daily intraperitoneal injections of AX059 starting from the first day of clinical symptoms, beginning on day 11; and AX115 starting from the first day of clinical peak (i.e., score 4), beginning of day 14. All inhibitors were administered for 2 weeks. The selectivity of the compounds for the different PLA$_2$s is shown as the percentage inhibition in Table 1. Their $X_f(50)$ values are also shown in Table 1. The $X_f(50)$ is the mole fraction of the inhibitor in the total substrate interface required to inhibit the enzyme by 50%.

Mouse Inflammation Antibody Array

Spinal cords were removed from vehicle and inhibitor treated animals when the vehicle-treated mice reached the peak of disease (score of 4). The tissues were then homogenized in lysis buffer and centrifuged at 1000×g. These protein samples were then assessed using the Raybio® inflammatory antibody array from RayBiotech Inc (Norcross, Ga.). Briefly, blocking buffer was added to glass-chip slides, which are coated with antibodies against chemokine, cytokine and related proteins. The slides were then incubated with the various protein samples from the treatment and control groups. After washing the glass slides, they were incubated sequentially with a biotin conjugated secondary antibody solution, horseradish peroxidase (HRP)-conjugated strepavidin, and HRP detection buffer. The signals were then visualized by chemiluminescence. Densitometric analysis was performed to detect differences between the various samples using ImageQuant 5.1 software (Molecular Dynamics). Positive control signals were used to normalize the level of expression from different glass slides being compared. Experiments were repeated with 3 different samples (n=3), and all the detection and analysis was done blind.

Lipid Profiling

Spinal cords were removed from vehicle and inhibitor treated animals at the peak stage of disease when the vehicle-treated mice reached the clinical score of 4, and the tissue snap frozen in liquid nitrogen. Lipid profiling was carried out by Lipomics Technology Inc. (West Sacramento, Calif.). The tissues were then extracted for either TrueMass® lipid profiling, or an eicosanoid inflammatory panel analysis. The lipids from the tissues were extracted in the presence of authentic internal standards as previously described (55), using chloroform:methanol (2:1 v/v). Individual lipid classes within each extract were separated by liquid chromatography (Agilent Technologies model 1100 Series). Each lipid class was trans-esterified in 1% sulfuric acid in methanol in a sealed vial under a nitrogen atmosphere at 100° C. for 45 min. The resulting fatty acid methyl esters were extracted from the mixture with hexane containing 0.05% butylated hydroxytoluene and prepared for gas chromatography by sealing the hexane extracts under nitrogen. Fatty acid methyl esters were separated and quantified by capillary gas chromatography (Agilent Technologies model 6890) equipped with a 30 m DB-88MS capillary column (Agilent Technologies) and a flame-ionization detector. Lipomic Surveyor® software was used to visualize changes within the treated groups. Experiments were repeated with 3 different samples (n=3), and all the detection and analysis was done blind.

Eicosanoid Analysis

Lipids extracted from tissues using solid phase extraction in the presence of a mixture of deuterium labeled surrogates. The mass of the sample and the surrogate standards were used to calculate the quantitative amount of each analyte in the test matrix. Each sample was analyzed by LC/MSMS, using Phenomenex Luna C18 reverse phase column (150×2.1 mm) connected to a Waters Quattro Premier triple quadrupole mass spectrometer. The analytes were ionized via negative electrospray and the mass spectrometer was operated in the tandem MS mode. An analytical software (MassLynx V4.0 SP4 2004, Waters Corporation) was used to identified target analytes based on the reference standard to generate a profile. Experiments were repeated with 3 different samples (n=3), and all the detection and analysis between treatment groups was done blind.

Statistical Analyses

Statistical analyses of the results of the functional assessments were performed by using two way repeated measures Friedman's ANOVA on Ranks. All other analyses were carried out using the student's T test. Differences were considered significant if $p<0.05$.

EXAMPLE 2

Animal Model of SCI—Spinal Cord Contusion and Drug Administration

All surgical procedures were approved by the McGill University Animal Care Committee and followed the guidelines of the Canadian Council on Animal Care. Adult (8-10 weeks old) female BALB/c (Charles River Canada), cPLA$_2$ GIVA$^{-/-}$ mice and wild type littermates were anesthetized with ketamine:xylazine:acepromazine (50:5:1 mg/kg). After performing a laminectomy at the 11$^{th}$ thoracic vertebrae, the exposed spinal cord was contused using the Infinite Horizons Impactor device (Precision Scientific Instrumentation, Lexington, Ky.). Moderate injuries were made using a force of 50 kDynes, and only animals that had tissue displacements ranging between 400-600 um were used.

EXAMPLE 3

Treatment of SCI by Inhibition of sPLA2 and/or iPLA$_2$ and/or cPLA$_2$

PLA$_2$ inhibitors. It has been previously reported that long chain 2-oxoamides based on gamma-amino acids are potent inhibitors of cPLA$_2$ (GIVA). While potent 2-oxoamide inhibitors of cPLA$_2$ (GIVA) containing a free carboxylic group do not inhibit iPLA$_2$ (GVIA), various 2-oxoamides containing ester groups inhibit both cPLA$_2$ (GIVA) and iPLA$_2$ (GVIA). A 2-oxoamide based on a glycine methyl ester, AX115, inhibits sPLA$_2$ (GV) as well as cPLA$_2$ (GIVA) and iPLA$_2$ (GVIA). The structure of AX115 as well as the activities against the three PLA$_2$ isoforms is provided in Table 1.

Compound AX115 was tested for its ability to inhibit human cPLA$_2$ (GIVA) in a cPLA$_2$ (GIVA) specific assay that uses mixed micelles of the substrate 1-palmitoyl-2-arachidonyl phosphatidylcholine and the detergent Triton X-100 (97:3) containing phosphatidylinositol 4,5-bisphosphate (400 µM) as previously described. The standard iPLA$_2$ (GVIA) activity assay utilizes DPPC/Trition X-100 mixed micelles at a ratio of 1:4.

GIIA PLA$_2$ is more difficult to assay in vitro because it does not work well on PC/Triton micelles. Vesicle assays have generally been employed for this enzyme, but they have limitations for in vitro comparison of inhibitor potency. However, experiments using a vesicle assay described above gave comparable inhibition for AX115 with GIIA and GV PLA$_2$.

PLA$_2$ inhibitor treatment. Mice were given daily intraperitoneal injections of 2 mM 2-oxoamide (sPLA$_2$ inhibitor; AX115) in 200 ul (6.85 mg/kg), starting 1 h after contusion and for 14 days. The control group that also had SCI were treated daily with vehicle.

RT-PCR. RNA from 5 mm length of spinal cord tissue containing the lesion site harvested at 1, 3, 7, 14, 21 and 28 dpi was extracted using RNeasy Lipid Tissue kit (Qiagen, Mississauga, Ontario, Canada). PCR amplification was performed with specific primers for mammalian PLA$_2$ family members. Peptidylprolyl isomerase A (PPIA) was used a control to ensure equal cDNA samples for PCR amplification. Six spinal cords were pooled for each time point.

Western blotting. Protein was extracted from 5 mm length of spinal cord tissue containing the lesion site harvested at the same time points that were used for the mRNA work. Protein samples (20 µg) were separated on a 4-12% Bis-Tris gel (Invitrogen) and transferred onto PVDF membranes (Millipore). The membranes were incubated with antibodies against cPLA$_2$ GIVA (Santa Cruz), iPLA$_2$ VIA (Cayman Chemical), sPLA$_2$ GIIA (Cayman Chemical) and bands were detected using Chemiluminescence (Western Lightning Chemiluminescence Reagent Plus, PerkinElmer). β-actin (Sigma Aldrich) was used to ensure equal loading of samples. Three samples were used for each time point Functional assessment. Locomotor recovery was evaluated in an open-field test using the Basso Mouse Scale (BMS), which was specifically developed for locomotor testing after contusion injuries in mice. The BMS analysis of hindlimb movements and coordination was carried out by two independent assessors who were trained in Michelle Basso's laboratory at Ohio State University, and the consensus score taken. The final score is presented as mean±SEM. The BMS is a compressed scale with a maximum score of 9 as compared to the 20-point BBB scale for rats. Therefore small differences in the BMS can account for larger functional differences.

Histology. Mice were perfused with 4% paraformaldehyde in 0.1M phosphate buffer (PB) at 1, 3, 7, 14 and 28 days post-lesion. 5 mm length of the spinal cord containing the lesion site was removed, cryoprotected with 30% sucrose in 0.1M PB, and cut in serial sections (16 µm thick). For double immunoflorescence, sections were incubated with antibodies against cPLA$_2$ GIVA (Santa Cruz), iPLA$_2$ GVIA (Cayman Chemical) or sPLA$_2$ GIIA (Cayman Chemical) and combined with antibodies against Mac-1 (for macrophages/microglia, Serotec), GFAP (for astrocytes, Zymed Labs), CCl (for oligodendrocytes, Calbiochem), NeuN (for neurons, 1:500, Chemicon) and SMI312 (for axons, Covance). Immunofluorescence labeling for 5-HT (Sigma, Aldreich) was also performed to assess innervation of serotonergic axons caudal to the lesion. In addition, one series of serial sections of the spinal cord were stained with Luxol fast blue (LFB) histochemistry, which stains myelin, and another series stained with cresyl violet histochemistry to quantify neuronal loss.

Quantification of histological results. Histological quantification was performed from spinal cord sections harvested at 28 dpi. Tissue sections were viewed with an Axioskop 2 Plus microscope (Zeiss) and images captured using a QImaging Retiga 1300 camera, and quantification done using BioQuant Nova Prime image analysis system (BioQuant Image Analysis Corp.). Tissue sparing was calculated by delineating the GFAP stained sections. Assessment of myelin sparing was performed by calculating the area occupied by myelin in the lateral funiculi. Neuronal survival was assessed by counting the neuron profiles in the ventral horn below the level of the central canal of the spinal cord in tissue sections stained with cresyl violet. Assessment of serotonergic innervation was performed by calculating the area occupied by serotonergic axons in the lateral funiculi and ventral horns of spinal cord sections taken at a distance of 1000 µm caudal to the lesion site.

Statistical analyses. Data are shown as mean±SEM. RT-PCR and Western blot analyses were done using one-way ANOVA with post-hoc Dunnett's test. Statistical analyses of the functional and histological assessments were performed by using two way repeated measures ANOVA with post-hoc Tukey's test for multiple comparisons. Differences were considered significant at $p<0.05$.

EXAMPLE 4

Animal Model of Multiple Sclerosis

Generation of EAE: EAE was induced in female SJL/J mice by subcutaneous injections of 100 pg of proteolipid protein (PLP) (Sheldon Biotechnology Centre, Montreal, Canada) in Complete Freund's Adjuvant (CFA) incomplete Freund's adjuvant containing 4 mg/ml of heat inactivated *Mycobacterium tuberculosis* (Fisher Scientific, Nepean, Canada)]. They were then boosted on day 7 with 50 µg of PLP in CFA containing 2 mg/ml of heat inactivated *Mycobacterium tuberculosis*. The mice were monitored daily for clinical symptoms of EAE using the following 5-point scale: Grade 0=normal (no clinical signs), Grade 1=flaccid tail, Grade 2=mild hindlimb weakness (fast righting reflex), Grade 3=severe hindlimb weakness (slow righting reflex), Grade 4=hindlimb paralysis, Grade 5=hindlimb paralysis and forelimb weakness or moribund. The clinical monitoring was done in a blind fashion.

EXAMPLE 5

Evaluation of EAE Animals Treated for MS

RT-PCR: Spinal cords and spleens were removed from animals at the onset, peak, and remission stages of disease, and RNA isolated using the RiboPure™ kit (Ambion Inc, Austin, Tex.) and reverse transcribed to cDNA. RT-PCR was performed using the GeneAmp RNA PCR kit (PerkinElmer Life Sciences). Primers used were as follows:

cPLA$_2$ U-5'-ATGCCGCCCGCCTGTCCTT-3', (SEQ ID NO: 1)

L-5'-GGGTCCTTGAGCCTCATCATCA-3'; (SEQ ID NO: 2)

sPLA$_2$ I IA, U-5'-AAGCGCCTGGAGAAAAGTGGATGT-3', (SEQ ID NO: 3)

L-5 GTGGGGCTGGGAGAGGTGTGAT-3' (SEQ ID NO: 4)

sPLA$_2$Y, U-5' CAACTGGAGGAAAAAGACTG-3', (SEQ ID NO: 5)

L-5'-CTTCCGGTCACAGGCACAGAGC-3'; (SEQ ID NO: 6)

GAPDH, U-5'-TGAAGGTCGGTGTGAACGGATTTGGC-3', (SEQ ID NO: 7)

L-5 CATGTAGGCCATGAGGTCCACCAC-3' (SEQ ID NO: 8)

PCR was performed with annealing temperatures of 55° C. (iPLA$_2$), 57° C. (cPLA$_2$ IVA, sPLA$_2$) and 60° C. (GAPDH).

EXAMPLE 6

Treatment Results: Multiple Sclerosis

Treatment of EAE-induced mice: EAE induced mice were randomly assigned to each of the treatment and control groups. For the groups that received treatment before the onset of clinical symptoms, treatment was started on day 6 after immunization and given daily for 3 weeks. Daily injections of the 2-oxoxamide compounds (AX006, AX059 or AX115) were given on a 3-day cycle consisting of one intravenous injection followed by 2 intraperitoneal injections. Mice in the control group were treated with PBS containing 5% Tween 80.

For the groups that received delayed treatment after symptoms occurred, mice were treated with daily intraperitoneal injections of AX059 starting from day 11 for 2 weeks. For the groups that received delayed treatment of the inhibitor AX115, the mice received daily intraperitoneal injections starting on the day the mice reached the first peak of the clinical attack. Treatment continued daily for a 2-week period.

PLA$_2$ isoforms are expressed differentially at various stages of EAE. We first assessed the mRNA expression of sPLA$_2$ (group HA and V) and cPLA$_2$ (group IVA) in the spleen and the spinal cord of SJL/J mice at the onset, peak and remission stages of EAE. mRNA expression was assessed by RT-PCR. The mRNA expression of cPLA$_2$ type IVA is increased at the onset of EAE in both the spleen and spinal cord (FIGS. 8, 9), suggesting it may play a role in initiation of the inflammatory changes in EAE. In contrast, the mRNA expression of sPLA$_2$ group HA and V are increased mainly in the peak and remission stages of EAE (FIGS. 8, 9), suggesting that these forms of sPLA$_2$ may play a role either in inhibiting inflammation during the remission phase or trigger another wave of inflammation that leads to the second clinical attack.

To assess the role of cPLA$_2$ (group IVA) in the onset and progression of EAE, SJL/J mice in which EAE was induced by immunization with a myelin peptide were treated. Mice were treated with two 2-oxoamide compounds specific for cPLA$_2$ (AX006 and AX059). These inhibitors were given intraperitoneally daily for 3 weeks starting on day 6 after the immunization, i.e, before the onset of clinical symptoms.

Mice were evaluated daily for clinical disability using the following 5-point scale: grade 0=normal; grade 1=flaccid tail; grade 2=mild hind limb weakness, quick righting reflex; grade 3=severe hind limb weakness, poor righting reflex; grade 4=hind limb paralysis; grade 5=hind limb paralysis and partial fore limb weakness. This analysis was done in a blinded fashion so the evaluator was unaware of the nature of the groups.

Figure 10A:
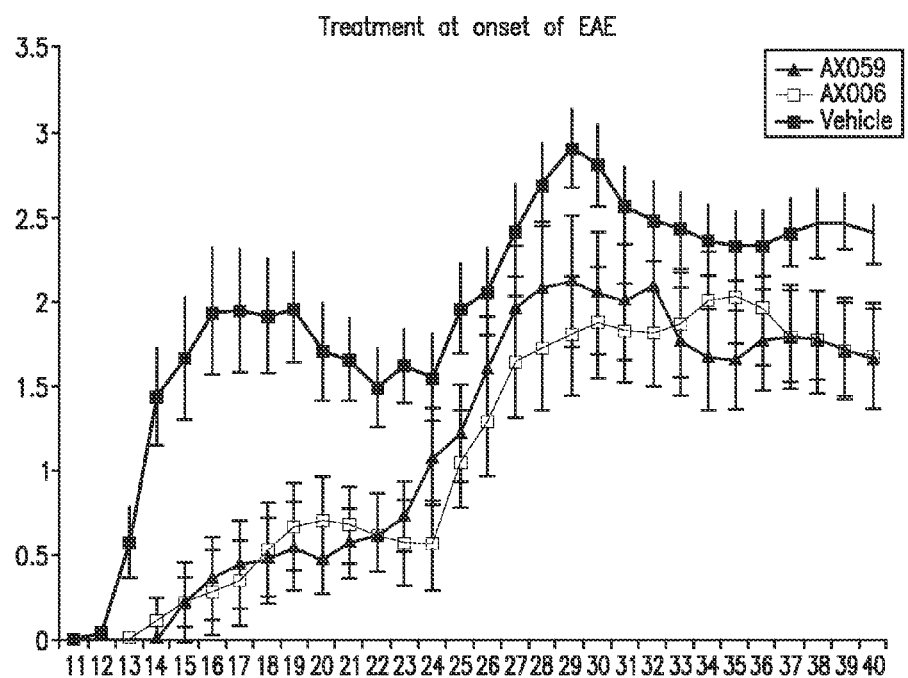
FIG. 10 is an illustration of the clinical course of SJL/J mice induced with EAE after treatment with inhibitors.

FIGS. 10 and 11 demonstrate some data illustrating the clinical course of SJL/J mice induced with EAE after treatment with inhibitors. FIG. 10A is a Graph showing the clinical course of SJL/J mice induced with EAE that were treated with two cPLA$_2$ specific inhibitors (AX059 and AX006) starting from day 6 for 3 weeks, compared to a vehicle treated EAE control (square). Data represent means±SEM from two independent experiments, with a total of 19 mice in each of the treated groups. The difference between cPLA$_2$ specific inhibitors and control groups is significant during the first paralytic episode (days 13 to 23; $P<0.01$), suggesting cPLA$_2$ has a role in initiation of disease.

Figure 10B:
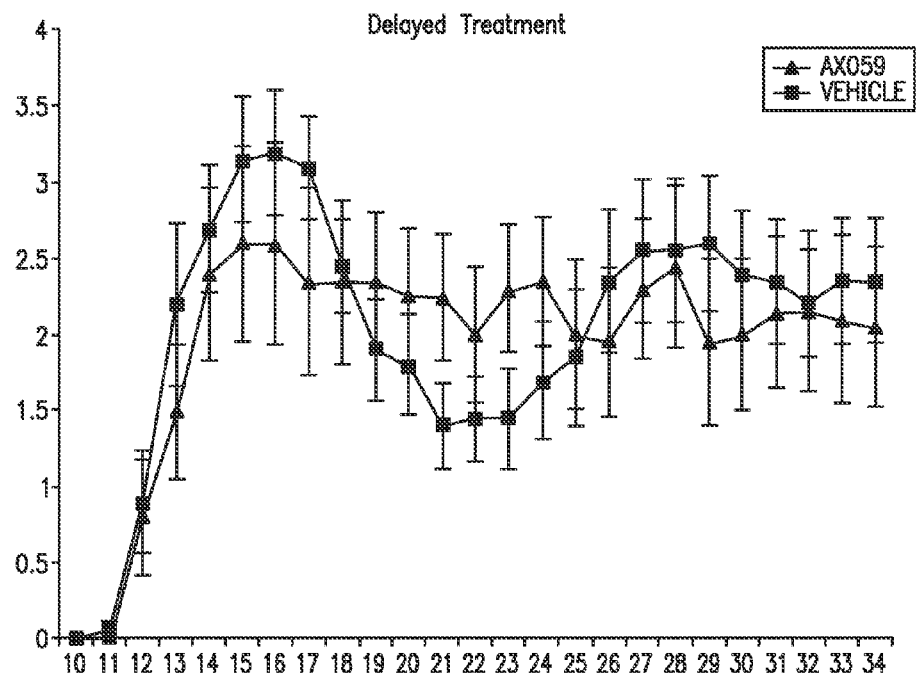

FIG. 10b is a graph showing the clinical course of SJL/J mice induced with EAE that were treated with the cPLA$_2$ specific inhibitor AX059, from the day mice began to show symptoms (day 11) for a 3 week period. There is no statistical significance between the cPLA$_2$ specific inhibitor treatment and control groups throughout the course of disease, suggesting that cPLA$_2$ does not play a role in progression of disease.

Figure 11A:
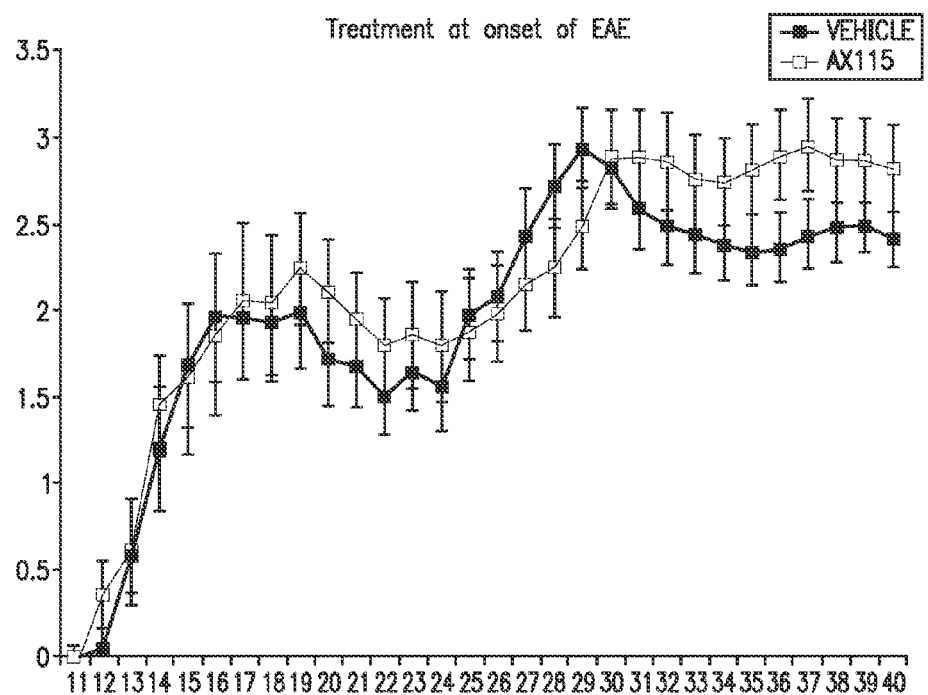
FIG. 11 is also an illustration of the clinical course of SJL/J mice induced with EAE after treatment with inhibitors.

FIG. 11a is a graph showing the clinical course of SJL/J mice induced with EAE that were treated with AX115 that has greater specificity for sPLA$_2$, compared to a vehicle treated EAE control (square). Data represent means±s.e.m from two independent experiments, with a total of 19 mice in each of the treated groups. There is no statistical significance between the two groups throughout the course of disease, suggesting that sPLA$_2$ does not play a role in initiation of disease.

Figure 11B:
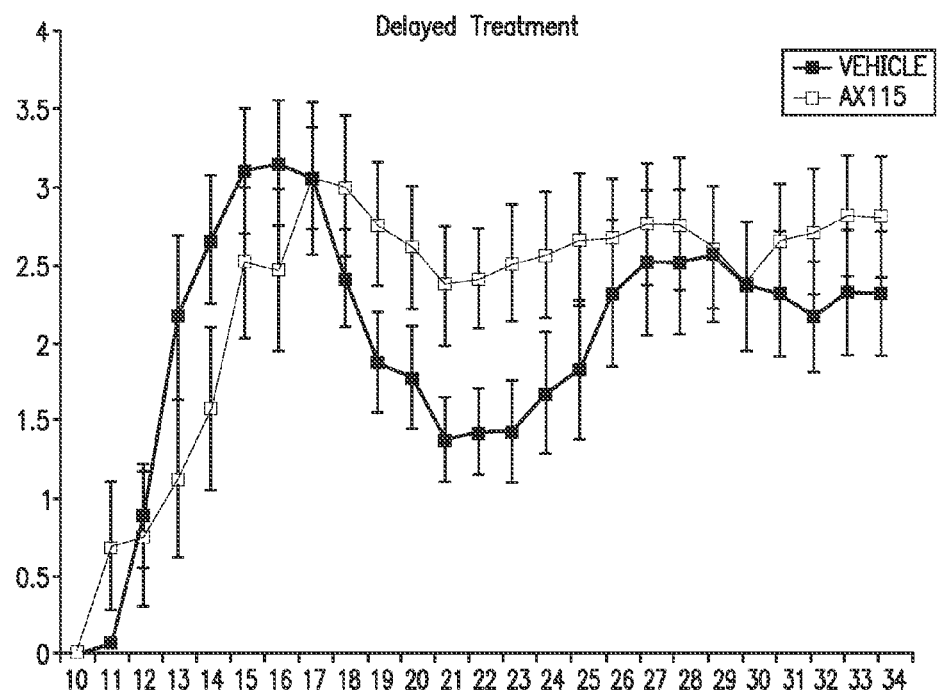

Finally, FIG. 11b is a graph showing the clinical course of SJL/J mice induced with EAE that were treated with AX115, from the day mice reached the peak of the first clinical attack (day 14), for a 3 week period. Inhibiting sPLA$_2$ with AX115 prevents remission of the disease. The difference between sPLA$_2$ specific inhibitor and control groups is significant during the remission phase (days 19 to 25; $P<0.05$), suggesting that sPLA$_2$ has a role in resolving inflammation.

Vehicle treated animals began to develop symptoms by day 11, and reached the first peak of clinical attack at day 18 with an average maximum clinical score of about grade 2 (FIG. 10a). The symptoms then remitted between days 20 and 25, followed by a second clinical attack which reached an average clinical score of grade 3 around day 30 (FIG. 10a). This was followed by a slight remission and the animals showed a clinical deficit of grade 2.4 at day 40. Mice treated with the cPLA$_2$ group IVA inhibitors AX006 and AX059 starting from day 6 after immunization to induce EAE, showed a significant reduction of disease severity in the early course of the disease, with a clinical score of only 0.5 at day 18, at which time the vehicle treated controls were at the peak of their first clinical attack (grade 2). Both groups of animals go into a second clinical attack around day 27, and at the termination of the experiment at day 40, the 2-oxoamides treated animals had reduced clinical disability with a score of 1.6 as compared to vehicle treated mice with a score of 2.4 (FIG. 10a). Since the treatments were stopped at day 27, it is possible that continued administration of the inhibitors may also reduce the severity of the second clinical attack.

When treatment was started after the onset of the clinical symptoms, i.e., day 11 after immunization and continued for 3 weeks, mice treated with AX059 showed a very modest reduction in the severity of the disease. AX059 treated mice reached a maximum grade of 2.5 at day 15, while the vehicle treated control group reached a mean score of 3.2 (FIG. 10b).

EXAMPLE 7

Inhibiting PLA$_2$ with 2-oxoamide AXII5 is Detrimental for EAE

Mice treated daily with the inhibitor AX115 starting on day 6 after immunization until day 27 did not differ from vehicle treated control mice in the onset and progression of the disease (FIG. 13B), suggesting that sPLA$_2$ does not play a significant role during the early stages of EAE. Since the mRNA studies showed that sPLA$_2$ group IIA and V are increased during the peak and remission phase, experiments were carried out to block sPLA$_2$ with AX115 starting from the time when the animals reached the peak of the first attack for a period of 2 weeks that includes the remission phase.

Mice treated with the sPLA$_2$ inhibitor AX115 displayed a mean maximal peak of about grade 3 at day 17, which did not differ from vehicle treated controls (id.). The vehicle treated mice progressed into a remission with an average score of about 1.4 at day 23. This remission was prevented in the AX115 treated mice, which had a clinical score of 2.5 on day 23 (id.). The AX115 treated mice also had a slightly more severe clinical score of 2.8 on day 35 as compared to a 2.3 in vehicle treated controls. This data suggest that sPLA$_2$ may play a role in initiating the remission stage in EAE, thus inhibiting sPLA$_2$ could be detrimental. These data therefore point to the importance of selectively blocking the appropriate PLA$_2$s for clinical treatments, which can vary in different neurological conditions.

EXAMPLE 8

Expression of PLA$_2$ Isoforms in EAE Mice

The results of this group of experiments are shown with the reference to FIG. 12. The legend on FIG. 12 is as follows:

(A) RT-PCR showing the changes in the expression of 4 PLA$_2$s (cPLA$_2$ GIVA, iPLA$_2$ GVIA, sPLA$_2$ GIIA and sPLA$_2$ GV) in the spinal cord (CNS) and spleen in normal mice, and at the onset, peak and remission stages of EAE.

(B) Quantification of the data in panel A showing the fold increase in mRNA expression at the onset, peak, and remission stages of EAE as compared to normal mice. Data presented as means±SEM from 3 mice (n=3).

(C) Graph showing the percentage of all immune cells expressing cPLA$_2$ GIVA, iPIA$_2$ GVIA, sPLA$_2$ GIIA and sPLA$_2$ GV in cells isolated from the CNS. Expression of all 4 PLA$_2$s is high in both onset and peak of disease, with subsequent reduction in the remission phase.

(D) FACS analysis data showing the percentage of different immune cell populations that express the 4 PI_A$_2$s from cells isolated from the CNS and spleen at different stages of EAE. Note that the numbers of positive cells is markedly higher in the CNS than in the spleen.

(E) Micrographs showing the ventral region of the lumbar spinal cord double-labeled with anti-GFAP and anti-PLA$_2$ antibodies that are indicated at the top of each panel.

As can be seen from the data presented by FIG. 12, PLA$_2$ isoforms are expressed differentially at various stages of EAE. The expression of PLA$_2$s in immune cell infiltrates in the submeningeal regions at the onset of disease, followed by a marked increase in all PLA$_2$s at the peak of disease. In the remission stage the expression of sPLA$_2$s still remains high. Scale bar=100 μm. Inserts show astrocytes labeled with cPLA$_2$ and sPLA$_2$. Scale bars in insets=30 μm.

Figure 12A:
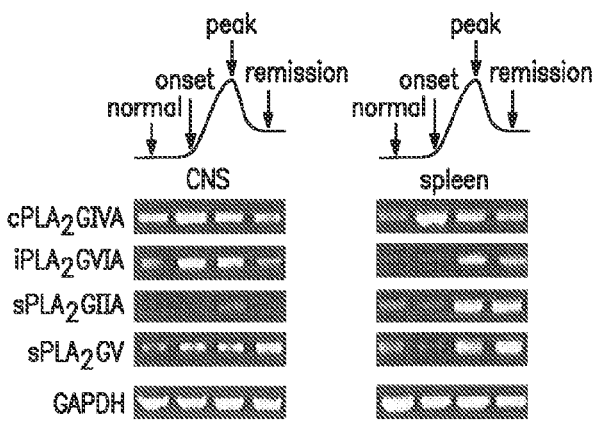
FIG. 12 is an illustration of expression of $PLA_2$'s in EAE.
Figure 12B:
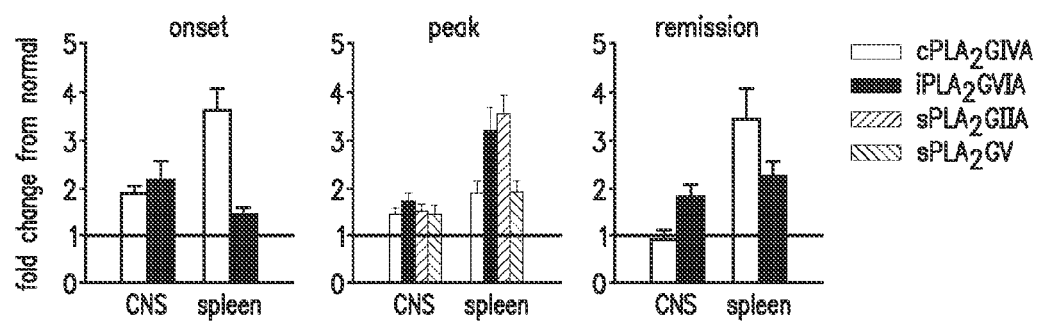

The mRNA expression of four intracellular PLA$_2$s was assessed first including calcium dependent (cPLA$_2$ [IVA, IVB]) and calcium independent (iPLA$_2$ [VIA, VIB]) forms, as well as ten sPLA$_2$s (IIA, IIC, IID, HE, IIF, V, VII, X, XII-1, XII-2) (FIG. 12a, data on the ones that did not change are not shown) in the spinal cord and spleen of SJL7J mice at the onset, peak and remission stages of EAE. The mRNA expression of cPLA$_2$ GIVA is increased mainly at the onset of EAE in the spinal cord and spleen (FIG. 12a, b), while iPLA$_2$ GVIA is increased at the onset and peak stages of the disease in the spinal cord, and highest at the peak in the spleen (FIG. 12a, b). In contrast, sPLA$_2$ is increased at the peak in the spinal cord and at the peak and remission stages in the spleen, while sPLA$_2$ is increased in the peak and remission stages in the spinal cord and spleen (FIG. 12a, b). Changes in the expression of these PLA$_2$s in the spinal cord are likely to be due to expression in the immune cells that are recruited and/or changes in expression by CNS glia in different stages of EAE.

Figure 12C:
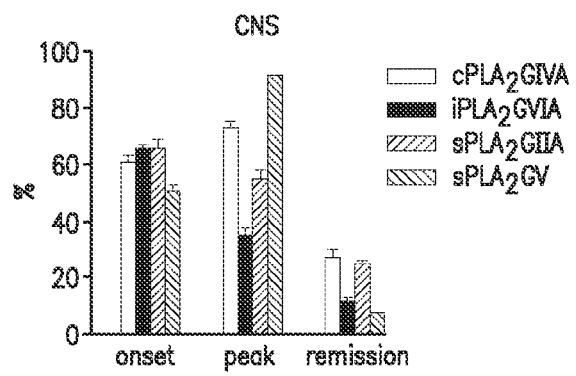
Figure 12D:
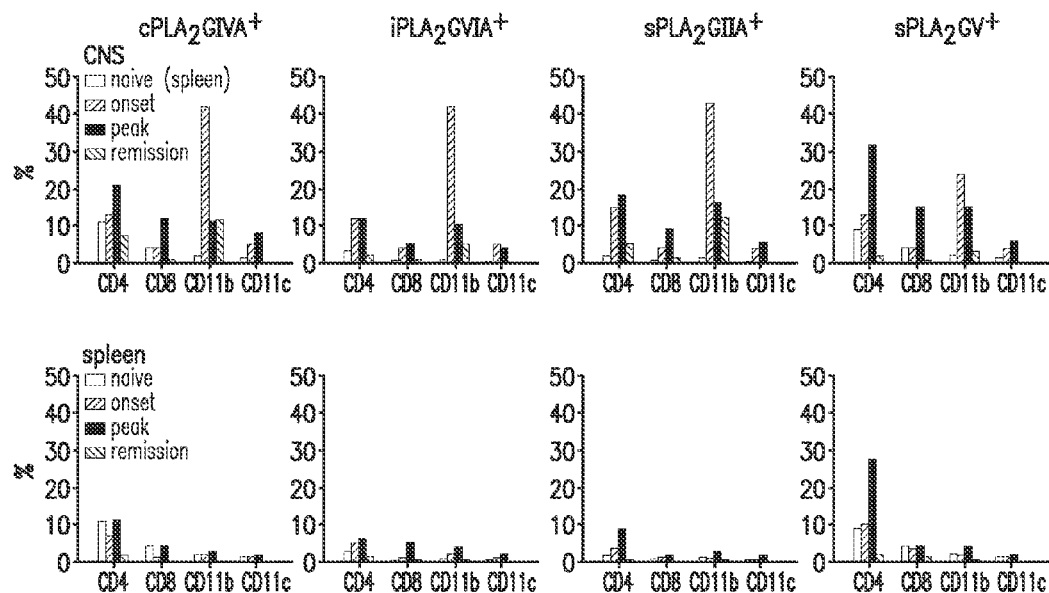

Next, experiments were conducted to evaluate changes in protein expression in immune cells. Protein expression of the four PLA$_2$s that showed changes at the mRNA level was assessed by fluorescence-activated cell sorting (FACS) analysis of immune cells isolated from the CNS and spleen from the onset, peak and remission stages (FIG. 12c, d). At the onset of EAE, when there is predominantly a macrophage infiltration (42%), followed by CD4$^+$ T cells (29%) (FIG. 12d), about 65% of all immune cells in the CNS express cPLA$_2$ GIVA, iPLA$_2$ GIVA and sPLA$_2$ GIIA, and 50% express sPLA$_2$ GV (FIG. 12c). This represents an increase of 1.8-fold for cPLA$_2$, 7.3-fold for iPLA$_2$, 8-fold for sPLA$_2$ GIIA and no increase in sPLA$_2$ GV based on baseline values obtained from immune cells in the spleen of naive mice. The expression of all four PLA$_2$s at the onset of EAE is predominately in CD11b$^+$ macrophages (FIG. 12d), followed by CD4$^+$ T cells, CD8$^+$ T cells and dendritic cells (FIG. 12d). At the peak stage, the proportion of T cells that express all four groups of PLA$_2$ increases (FIG. 12d). In the remission stage, cPLA$_2$ IVA and sPLA$_2$ IIA are expressed mainly by macrophages. Overall, all PLA$_2$s are expressed at much lower levels in the spleen than in the CNS (FIG. 12d).

Collectively, these data indicate that there is a marked increase in the proportion of macrophages and T cells that express the four PLA$_2$s after they enter the CNS in EAE, as compared to their initial site of activation in the spleen.

Figure 12E:
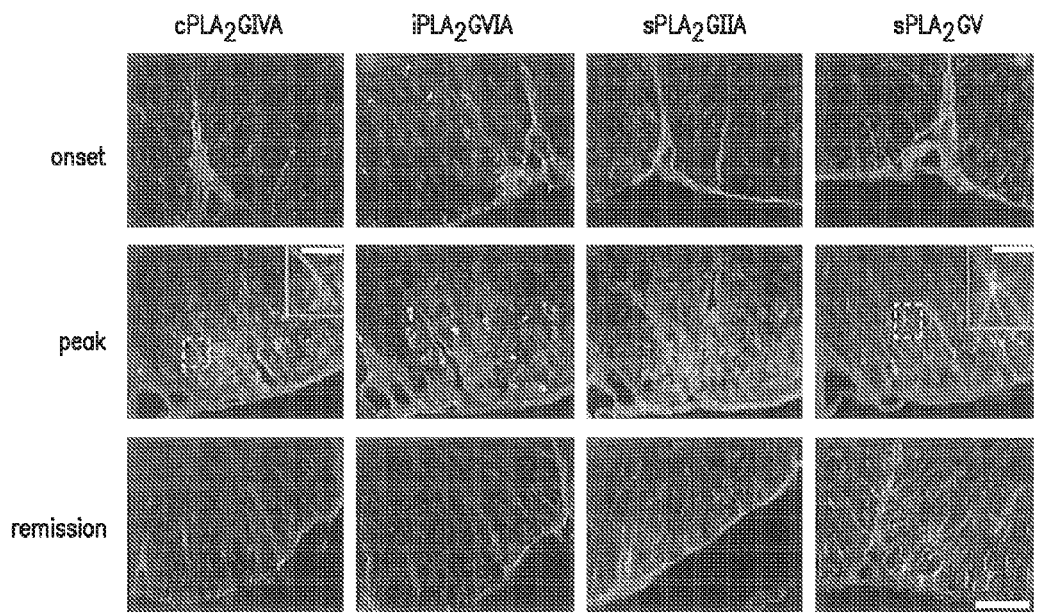

Next, experiments were conducted to evaluate changes in immunofluorescence staining of spinal cord tissue. In naive mice, there is low constitutive expression of all four PLA$_2$s in some astrocytes and oligodendrocytes in the spinal cord white matter (data not shown). At the onset of disease, all four PLA$_2$s are expressed in infiltrating immune cells (FIG. 12e), the details of which were assessed by FACS. Interestingly, in tissue sections, iPLA$_2$ GVIA is expressed mainly in infiltrating immune cells at the peak stage (FIG. 12e), while cPLA$_2$ GIVA, and sPLA$_2$ GIIA and GV, also show increased expression in astrocytes (FIG. 12e), and some oligodendrocytes. There is also a more diffuse immunoreactivity for the two sPLA$_2$s in regions of EAE lesions at the peak stage of EAE (FIG. 12e), suggestive of staining of secreted protein. In the remission stage, the expression of sPLA$_2$ GV in particular remains high in astrocytes (FIG. 12e).

EXAMPLE 9

Evaluation of the Role of PLA$_2$ Proteins in the Initiation of EAE

The results of this group of experiments are shown with the reference to FIG. 13 and Table 1 above. FIG. 13 includes the graphs showing the clinical course of EAE in SJL/J mice that were treated with a cPLA$_2$ inhibitor (AX059) (A), and a weak pan-PLA$_2$ inhibitor (AX115) (B). The data demonstrate effects of the inhibitor treatment started before the onset of symptoms can be seen as follows.

These inhibitors were administered before the onset of symptoms starting from day 5 to day 25; the EAE controls received vehicle injections (black circles). Data represent means±SEM; n=19 mice in each group. As seen on FIG. 13A, the difference between cPLA$_2$ selective inhibitor and control groups is significant during the first paralytic episode (days 13 to 23; P<0.01), suggesting that cPLA$_2$ has a role in initiation of disease.

The experiments were conducted to assess the role of the PLA$_2$ family members that showed increased expression in EAE, in initiating disease, i.e., onset of EAE, using two classes of small molecule inhibitors. cPLA$_2$ GIVA was blocked using a 2-oxoamide compound (AX059) that is a very highly selective and potent inhibitor of cPLA$_2$ GIVA (see also Table 1, above). Another pan-inhibitor that blocks PLA$_2$s was also used, i.e. a 2-oxoamide (AX115). (Table 1). The percentage inhibition shown in Table 1 denotes the selectivity of these compounds for the different PLA$_2$s tested. Their potency expressed as X$_I$(50) values are shown in Table 1. Inhibitors were administered daily for 3 weeks starting 5 days after the immunization, i.e., before the onset of clinical symptoms (~day 12).

Figure 13A:
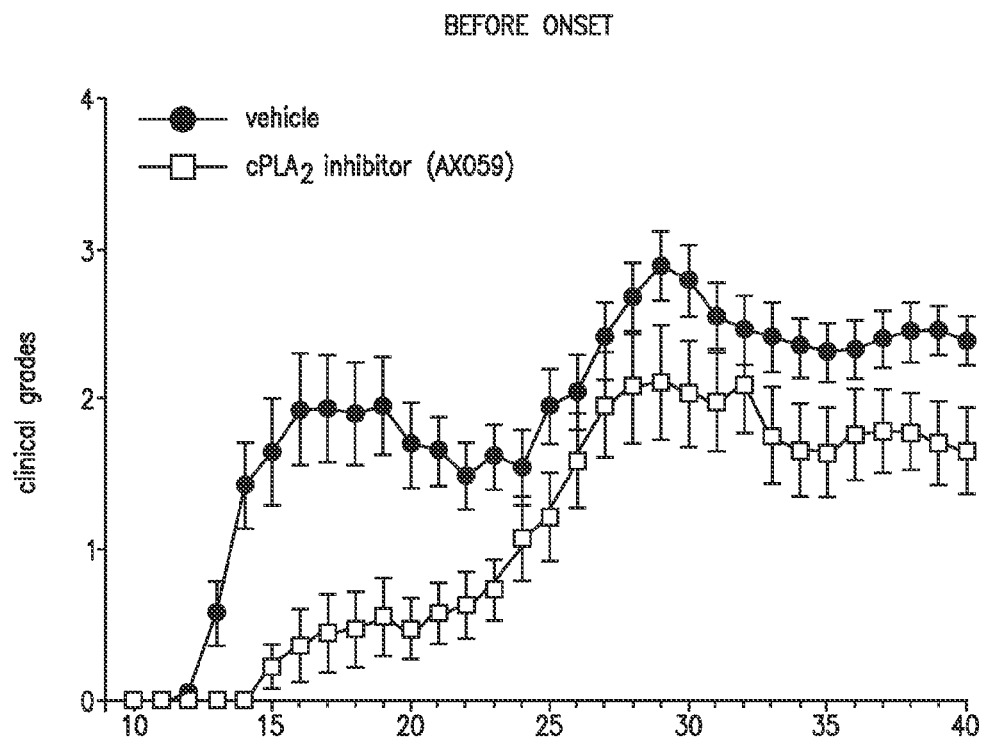
FIG. 13 is an illustration of effects of $PLA_2$'s inhibitor treatment started before the onset of symptoms.
Figure 13B:
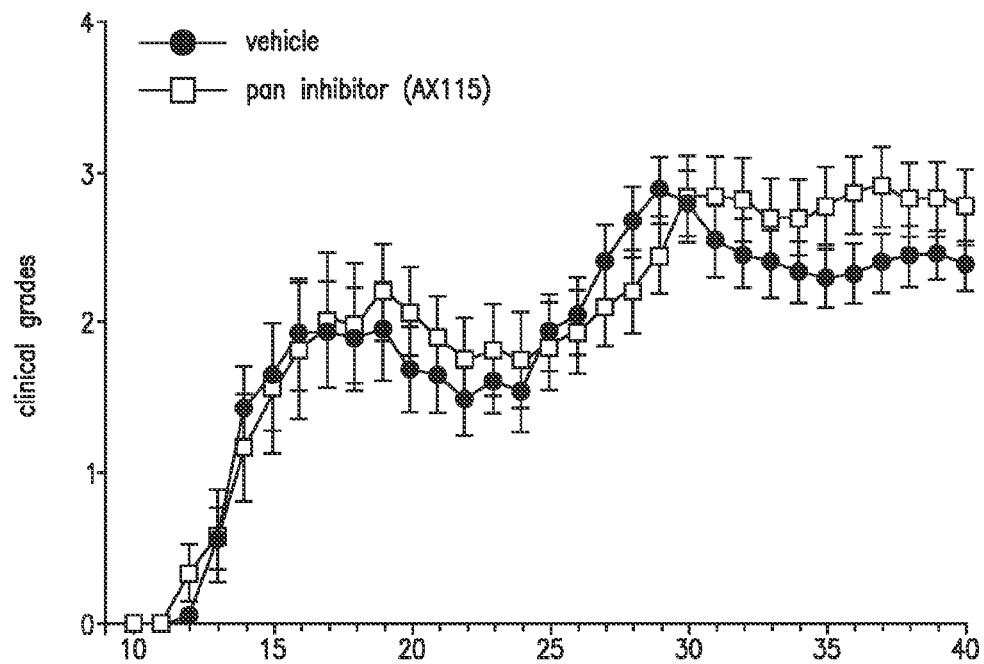

Mice were evaluated daily for clinical disability using a 5-point scale. Mice treated with the cPLA$_2$ GIVA inhibitor AX059, showed a significant reduction in the severity of early course of the disease (FIG. 13a), with abrogation of the first attack (clinical score of 0.5 at day 18), but progressing into a second attack at day 27. The end point disability score at day 40 was also lower than that of control EAE mice (FIG. 13a). Mice treated with AX115 did not substantially differ from vehicle treated controls (FIG. 13b).

Figure 14A:
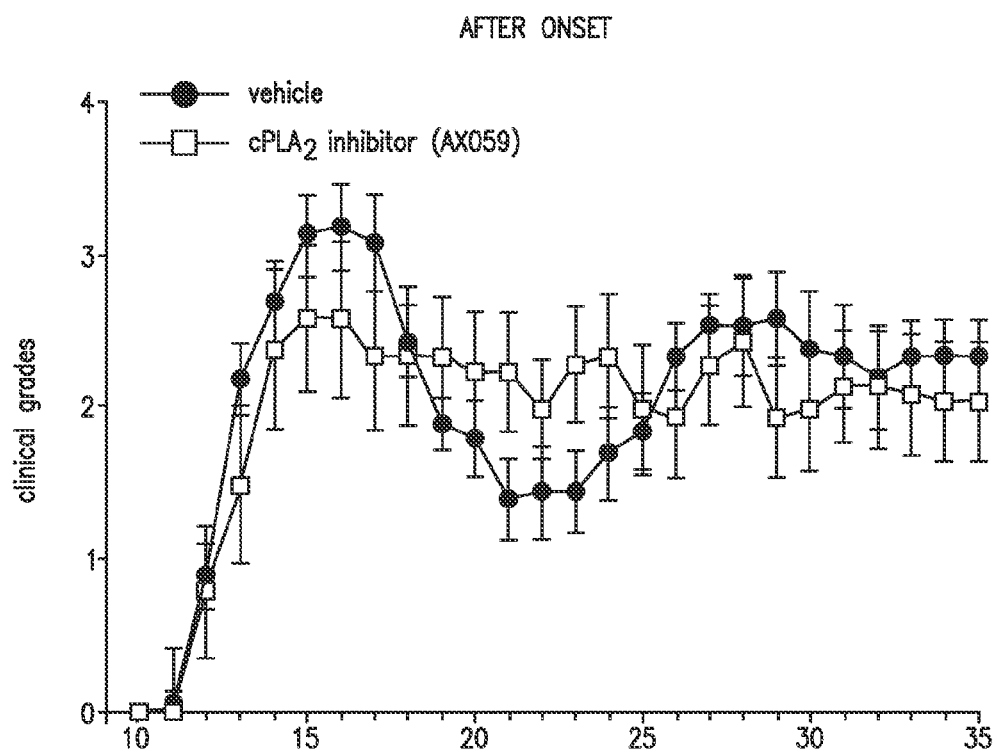
FIG. 14 is an illustration of effects of $PLA_2$'s inhibitor treatment started after the onset of symptoms.
Figure 14B:
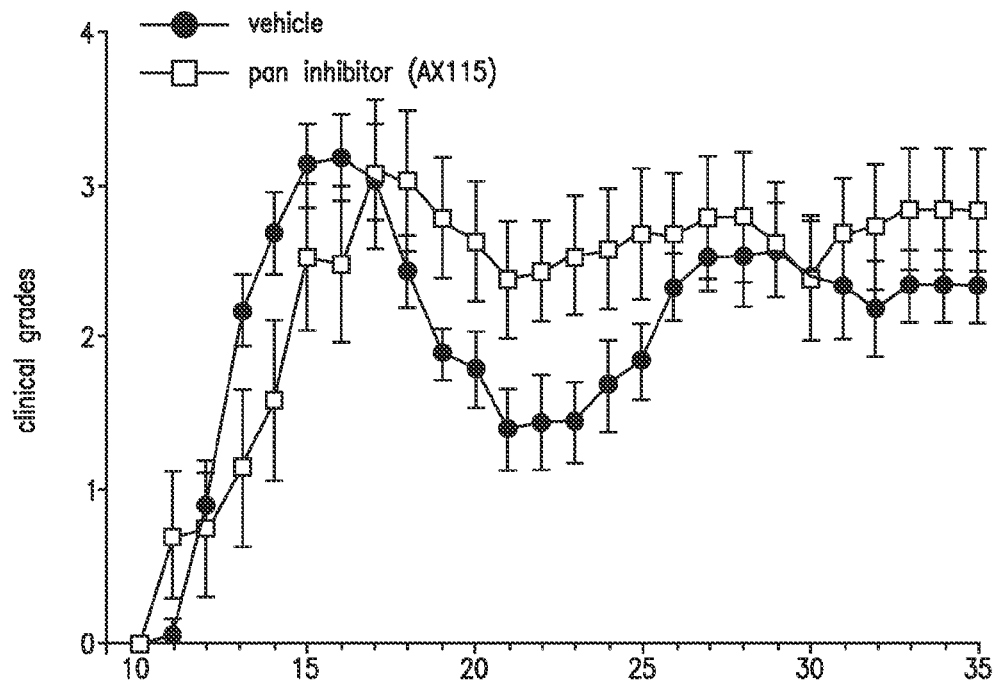

To further assess the roles of PLA$_2$ proteins in the progression of EAE, inhibitor treatments were started after the onset of clinical symptoms, i.e., day 11 after immunization, and continued for 2 weeks. Animals treated with the cPLA$_2$ selective inhibitor (AX059) show slightly reduced scores but these differences are not statistically significant from the controls (FIG. 14a), suggesting that although the cPLA$_2$ plays a role in the onset of the disease (FIG. 13a), it may not be important after the disease has been initiated, i.e., not in the progression phase. Treatment with AX115 worsened the disease, i.e., prevented the remission phase. On day 17, mice treated with AX115 had a mean peak score of grade 3, which did not differ from vehicle-treated EAE group (FIG. 14b). The vehicle treated mice progressed into remission with an average score of about 1.4 at day 23, while the AX115 treated mice had a worse clinical score of 2.5 (FIG. 14b). By day 35, the AX115 treated mice and vehicle treated EAE controls had a clinical score of 2.8 and 2.3, respectively.

EXAMPLE 10

Figure 15A:
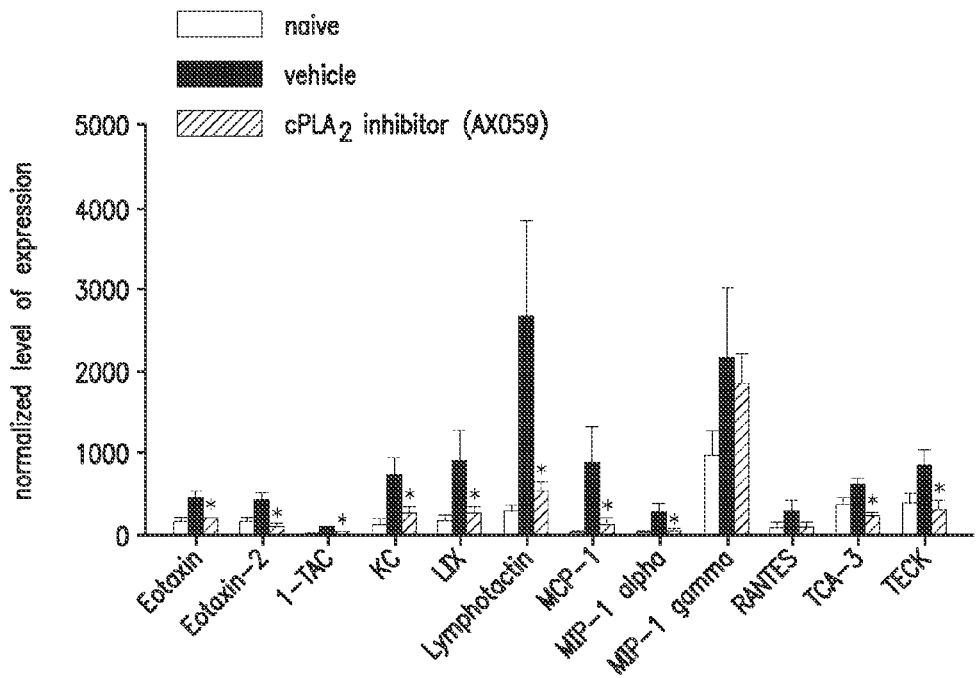
FIG. 15 is an illustration of changes in chemokine protein expression in $PLA_2$ inhibitor treated mice.
Figure 15B:
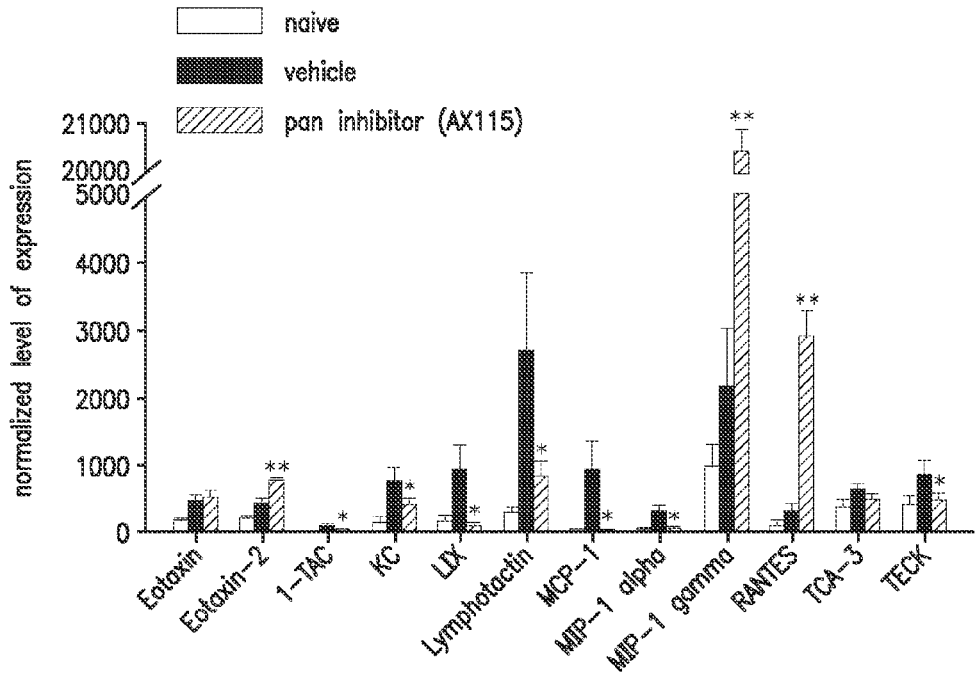

Evaluation of the Effects of PLA$_2$ Inhibitors on Chemokine and Cytokine Expression in EAE Mice The results of this group of experiments are shown with the reference to FIGS. 15 and 16. FIG. 15 provides graphs showing the level of protein expression of chemokines in spinal cords of naive mice and EAE mice treated with PLA$_2$ inhibitors starting on day 5. Tissues were taken on day 18, when the vehicle treated animals reached the peak of the first clinical attack. The data are shown for inhibitors AX059 (FIG. 15a) and AX115 (FIG. 15b). Data represent means±SEM from 3 animals in each group. In the figures, * represents a significant decrease, while ** represents a significant increase as compared to vehicle treated EAE controls.

Figure 16A:
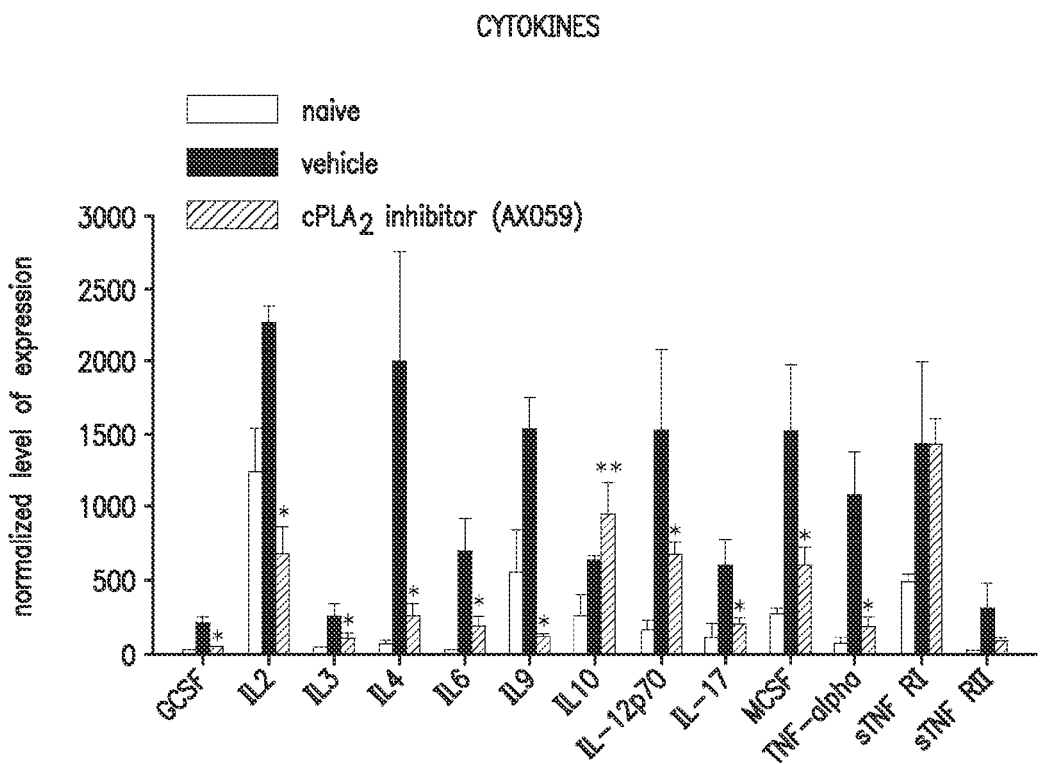
FIG. 16 is an illustration of changes in cytokine protein expression in $PLA_2$ inhibitor treated mice.
Figure 16B:
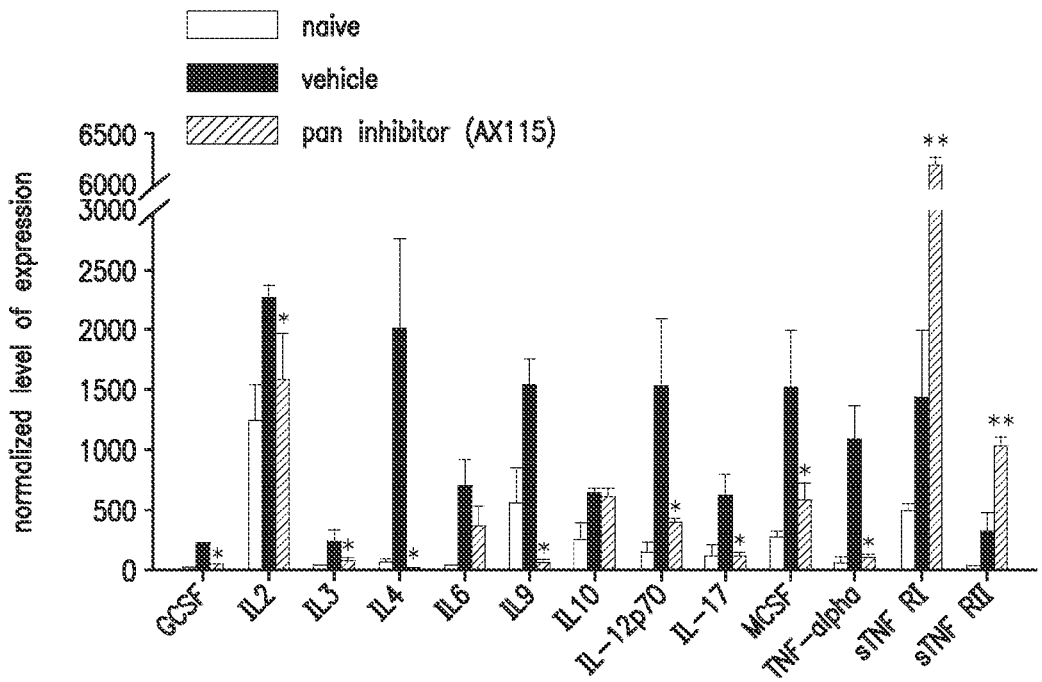

FIG. 16 provides graphs showing the level of protein expression of cytokines in spinal cords of naive mice and EAE treated mice treated with PLA$_2$ inhibitors starting on day 5. Tissues were taken on day 18, when the vehicle treated animals reached the peak of the first clinical attack. The data are shown for inhibitors AX059 (FIG. 16a) and AX115 (FIG. 16b). Data represent means±SEM from 3 animals in each group. In the figures, * represents a significant decrease, while ** represents a significant increase as compared to vehicle treated EAE controls.

Changes were assessed in protein expression of 40 chemokines and cytokines, their receptors and related molecules, using a mouse antibody array (RayBiotech Inc.). The analysis was carried out on spinal cords from mice treated with inhibitors starting from day 5 post-immunization. Tissue was taken on day 18 when the control vehicle-treated mice reached the peak of the first clinical attack. 12 chemokines were increased in vehicle-treated mice (FIG. 15), most of which are known to play a role in EAE, except for LIX (CXCL5) and TECK (CCL25), whose functions in CNS autoimmune disease remain unclear. AX059 inhibitor reduced 10 of the 12 chemokines that increase in vehicle-treated mice (FIG. 15A), indicating that it prevenst the robust inflammatory cascade seen in EAE. In contrast, the pan-inhibitor AX115, which inhibits sPLA$_2$ greater than AX059 reduced the expression of 7 of the 12 chemokines (FIG. 15b). Importantly, it increased the expression of eotaxin-2 (1.8-fold), RANTES (9.6-fold) and MIP-1 γ (9.7-fold) (FIG. 5c), which can also regulate the allergic arm of the immune response.

Similar profiling of cytokine protein expression revealed that 13 cytokines and related molecules were increased in vehicle-treated EAE mice (FIG. 16), all of which have been shown to play a role in EAE. AX059 inhibitor reduced expression of 11 of the 13 pro-inflammatory cytokines (FIG. 16a), as well as increased the expression of the anti-inflammatory cytokine IL-10 (~1.5-fold; FIG. 16a). AX115 on the other hand reduced expression of 9 of the 13 cytokines, failed to increase IL-10 (FIG. 16b), but caused a marked increase in soluble TNF receptor 1 (sTNFR1) (~4-fold) (FIG. 16b).

EXAMPLE 11

Evaluation of the Effects of PLA$_2$ Inhibitors on Differential Inhibition and Hydrolysis of Fatty Acids As PLA2s hydrolyze fatty acids from the sn-2 position of phospholipids, a comprehensive profiling was carried out of 40 fatty acids (FAs) that are attached to 5 phospholipid classes in extracts of spinal cords of naive mice, EAE mice treated with vehicle, and PLA2 inhibitor-treated EAE mice. This analysis shows the extent of different fatty acids that are released from the phospholipids classes in the different experimental and control groups as compared to naive normal spinal cord. These tissues were taken from the same groups of mice used for the chemokine/cytokine assay described above.

Changes in Vehicle-Treated EAE Mice

Vehicle-treated EAE mice showed increased hydrolysis and release of 11 FAs from the phosphatidylcholine (PC), cardiolipin (CL), and phosphatidylethanolamine (PE) classes for a total of 18 FA/phospholipid combinations, as compared to naive animals (see Table 2 showing the mean±SD of the fatty acid hydrolysis data, n=3 in each group. P<0.05 (student t-test)).

to CNS inflammation, as well as the release of protective FAs that may underlie remission that have not previously been considered in EAE.

TABLE 2

Fatty Acid Hydrolysis

| | Naive (nmol) | Treatment (nmol) | % Difference | P-value |
|---|---|---|---|---|
| Vehicle-treated EAE vs Naive | | | | |
| Cardiolipin - palmitic | 3122.3 ± 371.7 | 2272.8 ± 111.9 | 27.2 | 0.03 |
| Cardiolipin - arachidic | 464.0 ± 69.4 | 278.8 ± 64.6 | 39.9 | 0.02 |
| Cardiolipin - eicosapentaenoic | 16.1 ± 4.8 | 5.3 ± 4.8 | 67.1 | 0.05 |
| Cardiolipin - docosadienoic | 34.1 ± 5.3 | 21.2 ± 5.1 | 37.3 | 0.03 |
| Phosphatidylcholine - stearic | 5723.5 ± 164.5 | 5349.8 ± 61.4 | 6.5 | 0.03 |
| Phosphatidylcholine - behenic | 115.8 ± 8.1 | 94.8 ± 3.1 | 18.2 | 0.02 |
| Phosphatidylcholine - vaccenic | 3978.5 ± 165.3 | 3423.4 ± 102.4 | 14.0 | 0.01 |
| Phosphatidylcholine - arachidic | 347.9 ± 20.1 | 249.9 ± 16.6 | 28.2 | 0.001 |
| Phosphatidylcholine - oleic | 13980.0 ± 393.1 | 1196.5 ± 550.6 | 14.4 | 0.001 |
| Phosphatidylcholine - eicosenoic | 1666.2 ± 46.4 | 1227.6 ± 47.3 | 26.3 | 0.001 |
| Phosphatidylcholine - erucic | 177.1 ± 7.8 | 127.7 ± 7.4 | 27.9 | 0.001 |
| Phosphatidylcholine - nervonic | 47.7 ± 4.2 | 37.5 ± 2.7 | 21.4 | 0.02 |
| Phosphatidylcholine - docosadienoic | 90.4 ± 10.7 | 66.9 ± 3.8 | 26.0 | 0.03 |
| Phosphatidylethanolamine - arachidic | 589.3 ± 43.4 | 464.8 ± 7.8 | 21.1 | 0.01 |
| Phosphatidylethanolamine - vaccenic | 2043.2 ± 138.8 | 1694.6 ± 111.7 | 17.1 | 0.03 |
| Phosphatidylethanolamine - erucic | 341.4 ± 16.2 | 267.7 ± 14.7 | 21.6 | 0.001 |
| Phosphatidylethanolamine - eicosapentaenoic | 45.2 ± 8.6 | 27.3 ± 5.2 | 39.6 | 0.05 |
| Phosphatidylethanolamine - docosadienoic | 25.7 ± 4.4 | 15.4 ± 1.0 | 39.9 | 0.03 |
| cPLA$_2$ inhibitor (AX059)-treated EAE vs Naive | | | | |
| No increase in release of fatty acids. Fatty acid hydrolysis restored to naive levels | | | | |
| pan inhibitor (AX115)-treated EAE vs Naive | | | | |
| Cardiolipin - arachidic | 464.0 ± 69.4 | 324.4 ± 27.5 | 30.1 | 0.04 |
| Cardiolipin - eicosapentaenoic | 16.1 ± 4.8 | 3.2 ± 5.5 | 80.3 | 0.03 |
| Phosphatidylcholine - arachidic | 347.9 ± 20.1 | 269.4 ± 24.9 | 22.5 | 0.01 |
| Phosphatidylcholine - eicosenoic | 1666.2 ± 46.4 | 1393.4 ± 52.5 | 16.4 | 0.001 |
| Phosphatidylcholine - erucic | 177.1 ± 7.8 | 177.1 ± 7.8 | 22.4 | 0.001 |
| Phosphatidylserine - tetracosahexanoic | 9.7 ± 0.8 | 6.4 ± 0.6 | 33.8 | 0.001 |
| Phosphatidylserine-1-enyl-octadecenoic | 217.4 ± 37.9 | 133.3 ± 32.5 | 38.7 | 0.04 |

Four of the FAs (stearic, palmitic, arachidic, and behenic acids) are saturated FAs, which have pro-inflammatory functions. Stearic and palmitic acid can induce the expression of IL-1β, IL-2, IFN-γ, and TNF-α. Palmitic acid is also able to induce the expression of IL-6 and activate T cells. Nervonic acid, which shows 22% and 28% release from PE and PC, respectively, plays a major role in myelin biosynthesis, and its release could lead to myelin damage. Nervonic acid is decreased in post mortem brain tissue from MS patients. Moreover, the release of 9 FAs from PC would lead to the generation of LPC, a potent demyelinating agent that can also induce chemokine/cytokine expression in the CNS.

Additionally, in vehicle-treated EAE mice there is a 67% release of eicosapentaenoic acid (EPA) (Table 2), which leads to the production of the series-3 prostaglandins and series-5 leukotrienes, and the E-series of resolvins, which have anti-inflammatory properties and could put the brakes on the inflammation at the peak stage of EAE and lead to the onset of remission seen in these animals. Collectively, these lipid profiling data reveal many lipid mediators that could contribute Changes in Lipid Profiles in cPLA$_2$ and Selective Inhibitor Treated Mice The cPLA$_2$ selective inhibitor (AX059) prevented the hydrolysis of all FAs from phospholipids that were increased in EAE and yields a similar lipid composition profile as naive animals. Only the cPLA$_2$ inhibitor was able to prevent the production of PGE$_2$, thromboxane B$_2$ (TXB$_2$), 11-HETE and 15-HETE that are proinflammatory. This is consistent with cPLA$_2$ being the main regulator of arachidonic acid release that gives rise to these eicosanoids.

EXAMPLE 12

Expression of iPLA$_2$ in MS

Figure 17A:
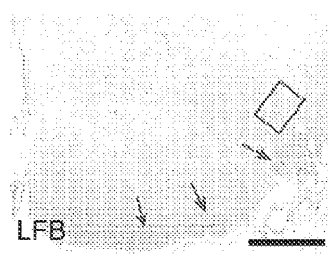
FIG. 17 is an illustration of expression of $iPLA_2$ in human MS.
Figure 17B:
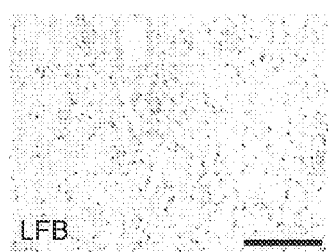
Figure 17C:
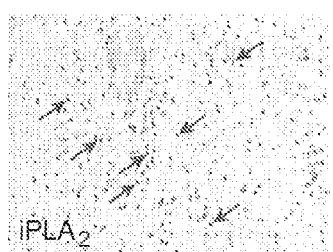
Figure 17D:
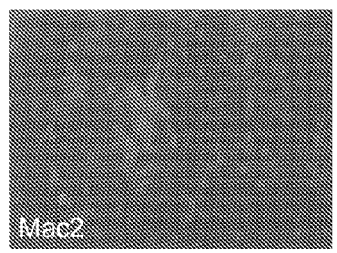
Figure 17E:
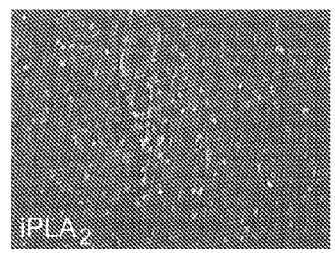
Figure 17F:
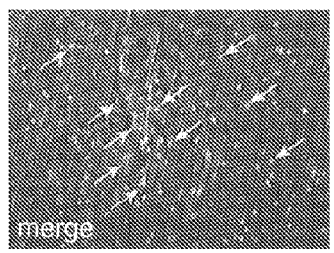

The expression of iPLA$_2$ in MS tissue was assessed. Interestingly, iPLA$_2$ positive immune cells were present in demyelinated regions of the CNS (FIG. 17a-c). In addition, iPLA$_2$$^+$ immune cells were also present in regions with active lesions as indicated by the presence of large numbers of macrophages (FIG. 17*d-e*). Some of these iPLA$_2$ cells are macrophages (FIG. 17*f*).

Indeed, FIG. 17*a* shows fentral funiculus of the spinal cord from a patient with secondary progressive MS stained with Luxol fast blue to visualize myelin which is seen mainly along the periphery of the section (arrows) and counterstained with hematoxylin. Note the loss of myelin in the ventral funiculus. FIGS. 17*b, c* show higher magnification of the area outlined by the rectangle in panel A. Tissue section stained with Luxol fast blue and hematoxylin (FIG. 17*b*) and iPLA$_2$ (FIG. 17*c*). Note the presence of iPLA$_2$ positive cells (arrows in C) in the area of the demyelinated lesion. Figs. d-f show double-immunofluorescence labelling for Mac-2 (activated macrophages) (FIG. 17*d*) and iPLA$_2$ (FIG. 17*e*) from an active lesion. Finally, FIG. 17*f* has, in the merged image, the presence of activated macrophages expressing iPLA$_2$ (arrows). Scale bars: A=3 mm, B-F=100 µm.

EXAMPLE 13

Further Evaluation of the Functional Role of cPLA$_2$ in SCI

The functional role of cPLA$_2$ in SCI was further assessed by comparing the effects of contusion injury in cPLA$_2$$^{-/-}$ mice and cPLA$_2$$^{+/+}$ littermates, and the discussion of the results is made with the reference to FIG. 7, where FIG. 7A shows, by RT-PCR, quantification of the changes in mRNA levels of cPLA$_2$ GIVA from 1 to 28 days after injury. FIG. 7B shows quantification of protein levels of cPLA$_2$ GIVA from 1 to 28 days after SCI detected by Western blotting. The activation of cPLA$_2$ protein is regulated by phosphorylation. Quantification of the two protein bands revealed that the activated form of cPLA$_2$ GIVA is significant up-regulated from 3 to 28 after SCI (*$p<0.05$).

Figure 7C:
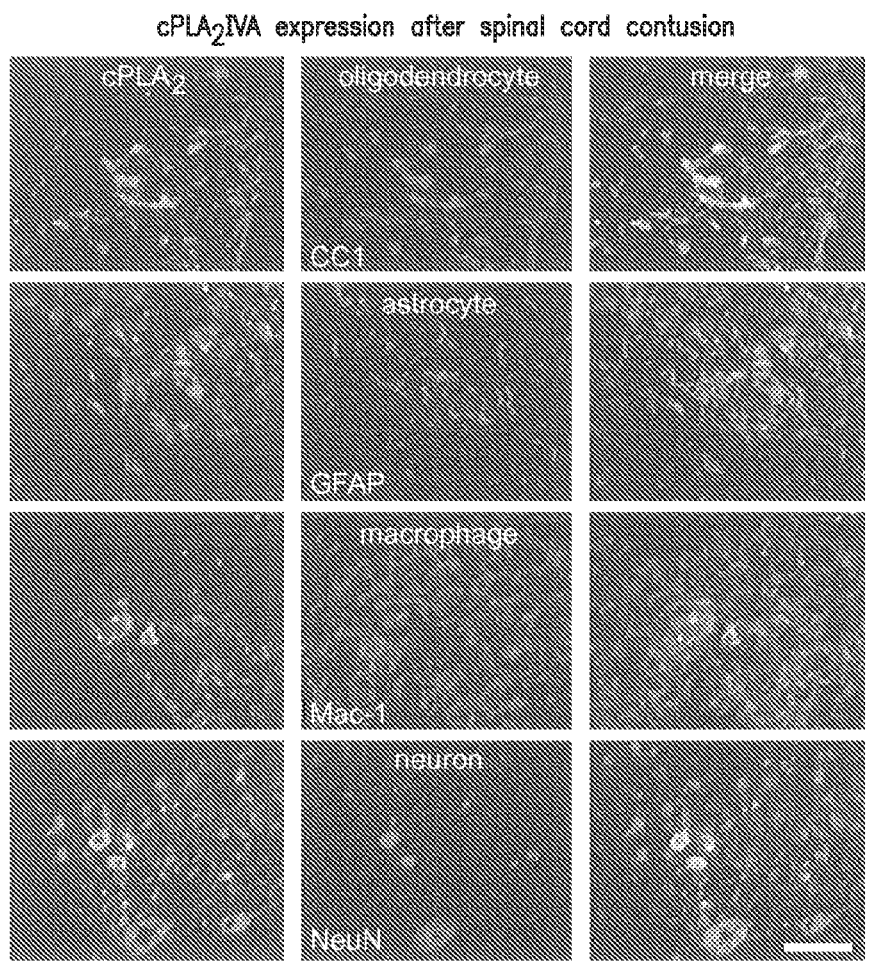
Figure 7D:
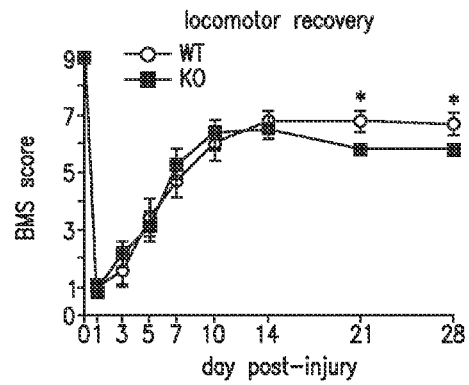
Figure 7E:
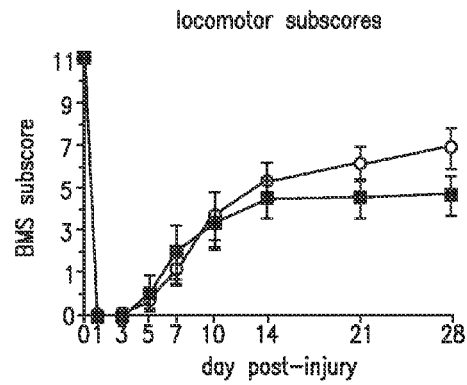
Figure 7F:
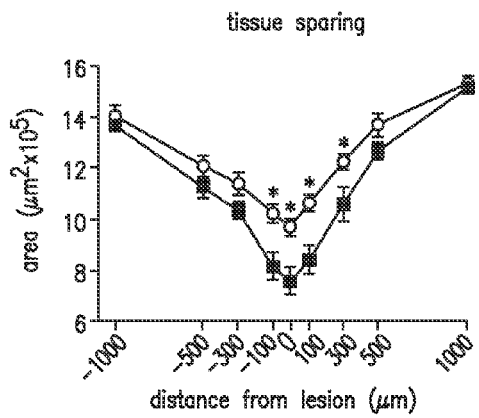
Figure 7G:
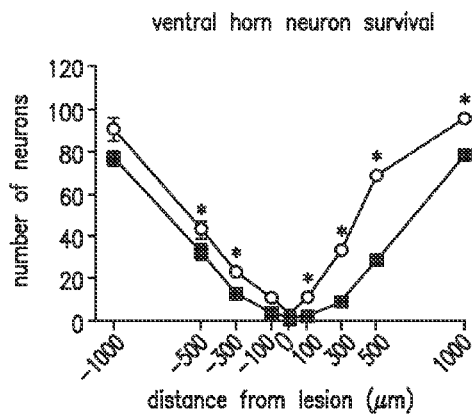

FIG. 7C shows double immunofluorescence images of cPLA$_2$ GIVA (green) co-labeled with anti-CC-1 (oligodendrocytes), anti GFAP (astrocytes), anti Mac-1 (macroglia/macrophages) and NeuN antibody (neurons). It may be noted that cPLA$_2$ GIVA is expressed in oligodendrocytes and neurons, but not in astrocytes or microglia/macrophages. FIGS. 7*d* and 7*e* show time course of locomotor recovery evaluated using the Basso Mouse Scale (BMS) (FIG. 7*d*) and locomotor BMS subscores (FIG. 7*e*). It may be observed that animals lacking cPLA$_2$ GIVA show significantly worse motor skills at 21 and 28 days after SCI in the BMS but not in the subscores (*$p<0.05$).

Figure 7H:
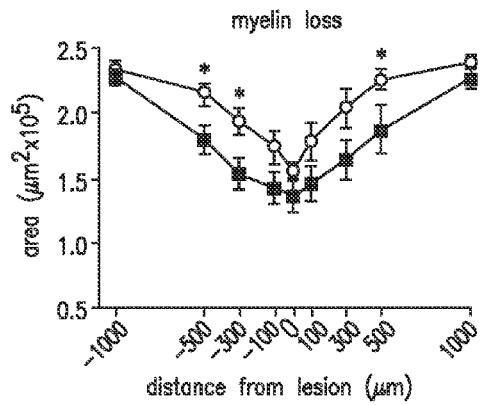

FIG. 7*f* shows quantification of tissue sparing assessed by staining for GFAP at 28 days after SCI. cPLA$_2$ GIVA1 mice display significant lost of tissue compared with wild type litermattes at the epicenter site and in adjacent areas ($p<0.05$). FIG. 7G illustrates veuron survival in the ventral horns assessed from tissue sections stained with cresil violet and FIG. 7H illustrates myelin sparing in the lateral funiculi assessed from sections stained with Luxol fast blue at 28 days after SCI. Animals lacking cPLA$_2$ GIVA display significantly greater loss of neurons and myelin in areas adjacents to the epicenter of the lesion ($p<0.05$). Bar=50 µm.

The data provided on FIG. 7 show that cPLA$_2$ mRNA is constitutively expressed in the uninjured spinal cord and is up-regulated about 2-fold at 3 days after SCI, and remained elevated until day 28 (FIG. 7*a*). The activation of cPLA$_2$ protein is correlated with phosphorylation of Ser$^{505}$ by MAPKs. The higher molecular weight band on Western blots that correspond to phospho-cPLA$_2$ is increased from 3 to 28 days post-injury (dpi) (FIG. 7*b*). The total cPLA$_2$ protein, however, remains unchanged (FIG. 7*b*). Double immunofluorescence labeling with cell type-specific antibodies revealed that at 3 dpi cPLA$_2$ is expressed in neurons and some oligodendrocytes located in areas adjacent to the lesion epicentre (FIG. 7*c*). It was, however, not expressed in macrophages/microglia or astrocytes.

Furthermore, locomotor recovery assessed using the 9-point Basso Mouse Scale (BMS) was worse in cPLA2$^{-/-}$ mice than in wildtype mice (FIGS. 7*d*, 7*e*). Histological analyses also revealed greater tissue and neuronal loss in cPLA$_2$$^{-/-}$ as compared to cPLA$_2$$^{+/+}$ mice. cPLA$_2$-deficient mice showed: (i) significant reduction in tissue sparing (FIG. 7*f*; (ii) significant reduction in the number of surviving ventral neurons (FIG. 7*g*); (iii) significantly greater myelin loss in areas adjacent to the lesion epicentre (FIG. 7*h*); and (iv) tissue cavitation, an unusual feature in mice SCI. Thus, the data indicate that cPLA$_2$ has a protective role after SCI.

EXAMPLE 14

Further Evaluation of the Functional Role of sPLA$_2$ after SCI Using Compound AX115

The functional role of sPLA$_2$ after SCI was further assessed by a 2-oxoamide compound of the present invention (AX115) that has greater selectivity for sPLA$_2$ than cPLA$_2$ and iPLA$_2$ (see, Table 1, above). The discussion of the results is made with the reference to FIGS. 2-5, where FIG. 2A shows quantification of the changes in mRNA levels of sPLA$_2$ GIIA from 1 to 28 days after SCI by RT-PCR.

FIG. 2B shows quantification of sPLA$_2$ group GIIA protein levels from 1 to 28 after SCI assessed by Western blotting. sPLA$_2$ GIIA is significantly up-regulated at 3 and 7 days after SCI. Although sPLA$_2$ GIIA antibodies may cross react with sPLA$_2$ GV, the lack of sPLA$_2$ GV mRNA in the spinal cord after SCI suggest us that the band observed in the Western blots for sPLA$_2$ GIIA is specific for this particular PLA$_2$ form. FIG. 3 shows quantification double immunofluorescence images of sPLA$_2$ GIIA (green) co-labeled with anti-CC-1 (oligodendrocytes), anti GFAP (astrocytes), anti Mac-1 (macroglia/macrophages), and NeuN antibody (neurons). sPLA$_2$ GIIA is mainly expressed in astrocytes and oligodendrocytes, although some microglia/macrophages and neurons also express it.

FIG. 4A is an illustration of time course of locomotor recovery evaluated by the BMS scores. Treatment with AX115 shows marked improvement in the BMS scores starting from 5 days after SCI. FIG. 4B also shows that AX115 treated mice a marked improvement in the finer aspects of locomotor control showing an increase of 4 points in the BMS subscores (*$p<0.05$), and FIG. 5A shows that AX115 treated animals show significant amount of tissue sparing at the lesion epicenter and adjacent regions (*$p<0.01$).

FIG. 5B demonstrates thats mice treated with AX115 have significantly greater neuron survival in regions ranging from 300 to 1000 µm rostral and caudal to the lesion epicenter (*$p<0.05$). Finally, FIG. 5C demonstrates thats mice treated with AX115 show a marked reduction of myelin loss in the epicenter and 300 mm rostral and caudal to the lesion site (*$p<0.01$), and FIG. 5D shows that animals treated with AX115 display significantly greater serotonergic innervation 1000 µM caudal to the lesion epicenter (*$p<0.05$). Bar=50 µm.

The data provided on FIGS. 2-3 show that sPLA$_2$ mRNA expression increased rapidly after SCI reaching ~100-fold by 28 dpi (FIG. 2a). Quantification of protein expression by Western blotting showed ~35-40 fold increase at 3 and 7 dpi (FIG. 2b). Many sPLA$_2$ immunoreactive cells were seen in white and grey matter at 3 and 7 dpi. In the grey matter, it was mainly expressed in astrocytes, some neurons and Mac-1$^+$ macrophages/microglia (FIG. 19c). sPLA$_2$ was expressed mainly in oligodendrocytes (FIG. 3) and some astrocytes and Mac1$^+$ cells in the white matter.

Daily administration of AX115 started 1 hour after injury markedly improved locomotor function as compared to vehicle treated injured mice. Post-hoc analysis revealed significant improvements in BMS scores beginning at 5 dpi, which remained significantly elevated for the duration of the experiment (FIG. 4a). By 28 days, the vehicle treated mice were able to step occasionally or frequently but without co-ordination or proper paw placement (score 4.6). In contrast, the AX115 treated mice displayed stepping with frequent co-ordination with proper placement of the paws (score 6.6). In addition, fine locomotor control evaluated by the BMS subscores showed a 4-point improvement with sPLA$_2$ inhibitor treatment (FIG. 4b).

Furthermore, treatment with the sPLA2 inhibitor (AX115) promoted: (i) significant tissue protection (FIG. 5a) and myelin sparing (FIG. 5c) at the lesion epicentre and adjacent areas; (ii) a 3-fold increase in the density of 5-HT fibers within the lateral funiculi and ventral horns (FIG. 5d); and (iii) significantly better survival of ventral horn neurons for distances of up to 1 mm rostral and caudal to the lesion (FIG. 5b). These data clearly demonstrate an important role of sPLA$_2$ in the evolution of the secondary pathology after SCI. sPLA$_2$ secreted by glial cells can degrade myelin because phosphatidylcholine is preferentially located on the outer side of the myelin membranes. LPC produced by the actions of sPLA$_2$ is also a potent demyelinating agent and at higher levels may cause axonal and neuronal damage. This is supported by the greater protection of 5HT axons and myelin, and the improved neuronal survival seen after SCI in mice treated with the sPLA$_2$ inhibitor.

Blocking enzymes downstream of PLA$_2$, such as COX-2 or 5-lipoxygenase, ameliorates only some of the detrimental effects of SCI. PLA$_2$ enzymes are therefore much better targets for therapeutic intervention. The results show the need to selectively target those PLA$_2$s that are detrimental (sPLA$_2$ and iPLA$_2$) in SCI while not altering others that are beneficial (cPLA$_2$). The inhibitor treatment is effective when initiated one hour after SCI, making this a therapeutically viable approach. Selective inhibitors of sPLA$_2$ and iPLA$_2$ such as the 2-oxoamide AX115, or related compounds, are likely to be excellent candidates for drug development for the treatment of acute SCI.

The inventions illustratively described herein may suitably be practiced in the absence of any element or elements, limitation or limitations, not specifically disclosed herein. Thus, for example, the terms "comprising", "including," "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims. In addition, where features or aspects of the invention are described in terms of Markush groups, those skilled in the art will recognize that the invention is also thereby described in terms of any individual member or subgroup of members of the Markush group. Further, the references appended hereto are all incorporated herein by this reference.

What is claimed is:

1. A compound selected from the group consisting of

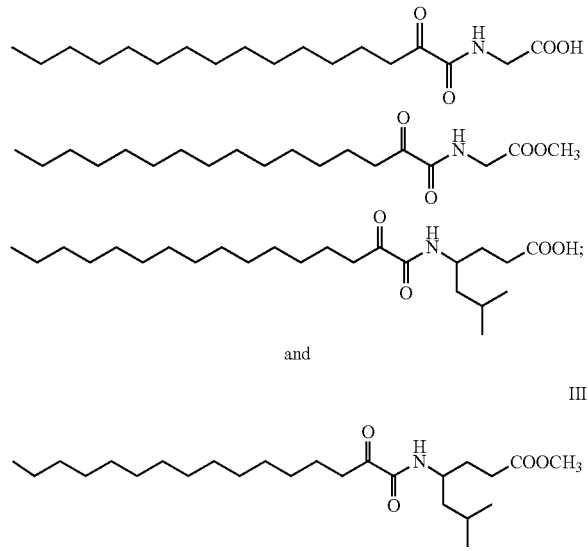

and enantiomeric forms or pharmaceutically acceptable salts thereof.

2. A method for inhibiting the enzymatic activity of phospholipase $A_2$ in a cell or organism, comprising contacting the cell or organism with a compound of claim 1, thereby inhibiting the enzymatic activity of phospholipase $A_2$.

3. The method of claim 2, wherein the enzymatic activity inhibited is phospholipase $iPLA_2$, $sPLA_2$, or $cPLA_2$.

4. A pharmaceutical composition comprising a compound of claim 1, and a pharmaceutically acceptable carrier.

5. A method for treating a disease or disorder associated with the enzymatic activity of phospholipase $A_2$, comprising administering to a patient in need thereof a pharmaceutically effective amount of a compound of claim 1 or a pharmacologically acceptable salt thereof, thereby inhibiting phospholipase $A_2$ and treating the disease or disorder.

6. The method of claim 5, wherein the disease or disorder is multiple sclerosis (MS) or spinal cord injury (SCI).

7. The method of claim 2, wherein the enzymatic activity inhibited is of phospholipase $cPLA_2$.

8. The method of claim 5, wherein the disease or disorder is spinal cord injury (SPI).

9. The method of claim 8, wherein the compound is a compound of structural formula I

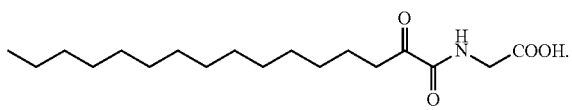

10. The method of claim 5, wherein the disease or disorder is multiple sclerosis (MS).

11. The method of claim 10, wherein the compound is a compound of structural formula III:

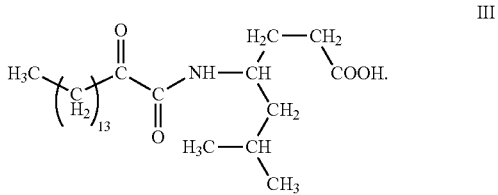

* * * * *

SEQUENCE LISTING

<160> NUMBER OF SEQ ID NOS: 8

<210> SEQ ID NO 1
<211> LENGTH: 19
<212> TYPE: DNA
<213> ORGANISM: Artificial sequence
<220> FEATURE:
<223> OTHER INFORMATION: Primer

<400> SEQUENCE: 1
atgccgcccg cctgtcctt                                              19

<210> SEQ ID NO 2
<211> LENGTH: 22
<212> TYPE: DNA

-continued

```
<213> ORGANISM: Artificial sequence
<220> FEATURE:
<223> OTHER INFORMATION: Primer

<400> SEQUENCE: 2
gggtccttga gcctcatcat ca                                                22

<210> SEQ ID NO 3
<211> LENGTH: 24
<212> TYPE: DNA
<213> ORGANISM: Artificial sequence
<220> FEATURE:
<223> OTHER INFORMATION: Primer

<400> SEQUENCE: 3
aagcgcctgg agaaaagtgg atgt                                              24

<210> SEQ ID NO 4
<211> LENGTH: 22
<212> TYPE: DNA
<213> ORGANISM: Artificial sequence
<220> FEATURE:
<223> OTHER INFORMATION: Primer

<400> SEQUENCE: 4
gtggggctgg gagaggtgtg at                                                22

<210> SEQ ID NO 5
<211> LENGTH: 20
<212> TYPE: DNA
<213> ORGANISM: Artificial sequence
<220> FEATURE:
<223> OTHER INFORMATION: Primer

<400> SEQUENCE: 5
caactggagg aaaaagactg                                                   20

<210> SEQ ID NO 6
<211> LENGTH: 22
<212> TYPE: DNA
<213> ORGANISM: Artificial sequence
<220> FEATURE:
<223> OTHER INFORMATION: Primer

<400> SEQUENCE: 6
cttccggtca caggcacaga gc                                                22

<210> SEQ ID NO 7
<211> LENGTH: 26
<212> TYPE: DNA
<213> ORGANISM: Artificial sequence
<220> FEATURE:
<223> OTHER INFORMATION: Primer

<400> SEQUENCE: 7
tgaaggtcgg tgtgaacgga tttggc                                            26

<210> SEQ ID NO 8
<211> LENGTH: 24
<212> TYPE: DNA
<213> ORGANISM: Artificial sequence
<220> FEATURE:
<223> OTHER INFORMATION: Primer

<400> SEQUENCE: 8
catgtaggcc atgaggtcca ccac                                              24
```